United States Patent [19]

Tao et al.

[11] Patent Number: 5,780,653
[45] Date of Patent: Jul. 14, 1998

[54] NITROPHENYL, 10-DEACETYLATED SUBSTITUTED TAXOL DERIVATIVES AS DUAL FUNCTIONAL CYTOTOXIC/ RADIOSENSITIZERS

[75] Inventors: Chunlin Tao; Neil P. Desai; Patrick Soon-Shiong; Paul A. Sandford, all of Los Angeles, Calif.

[73] Assignee: Vivorx Pharmaceuticals, Inc., Santa Monica, Calif.

[21] Appl. No.: 485,496

[22] Filed: Jun. 7, 1995

[51] Int. Cl.⁶ .................. C07D 305/00; C07D 413/00; C07D 233/02; A61K 51/04
[52] U.S. Cl. .................. 549/510; 514/449; 514/397; 544/60; 544/147; 544/162; 544/379; 548/311.4; 549/473; 424/1.65
[58] Field of Search .................. 549/510, 473; 514/449, 397; 424/1.65; 548/311.4, 328.5; 544/60, 147, 162, 379

[56] References Cited

U.S. PATENT DOCUMENTS

| | | | |
|---|---|---|---|
| 5,175,315 | 12/1992 | Holton | 549/510 |
| 5,250,683 | 10/1993 | Holton et al. | 544/60 |
| 5,283,253 | 2/1994 | Holton et al. | 514/444 |
| 5,399,726 | 3/1995 | Holton et al. | 549/510 |
| 5,556,878 | 9/1996 | Kelly et al. | 514/449 |

OTHER PUBLICATIONS

Carboni et al., *J. Med. Chem.*, vol. 36, 1993, pp. 513–515.

Chen et al., *Bioorg. Med. Chem. Let.*, vol. 4, No. 3, 1994, pp. 479–482.

Adams and Cooke, "Electron–affinic sensitization I. A structural basis for chemical radiosensitizers in bacteria" *Int. J. Radiat. Biol.* 15(5):457–471 (1969).

Brown, J.M., "Evidence for acutely hypoxic cells in mouse tumours, and a possible mechanism of reoxygenation" *Br. J. Radiology* 52:650–656 (1979).

Chaudhary et al. "Unexpectedly Facile Hydrolysis of the 2–Benzoate Group of Taxol and Syntheses of Analogs with Increased Activities" *J. Am. Chem. Soc.* 116:4097–4098 (1994).

Churchill–Davidson et al., "High–Pressure Oxygen And Radiotherapy" *Lancet* 1091–1095 (1955).

Commercon et al., "Improved Protection and Esterification of a Precursor of the Taxotere and Taxol Side Chains" *Tetrahedron Letters* 33(36):5185–5188 (1992).

Crissman et al., "Improved Response and Survival to Combined Cisplatin and Radiation in Non–Keratinizing Squamous Cell Carcinomas of the Head and Neck" *Cancer* 59(8):1391–1397 (1987).

Denis and Greene, "A Highly Efficient, Practical Approach to Natural Taxol" *J. Am. Chem. Soc.* 110:5917–5919 (1988).

Dorie et al.. "Comparison of the Enhancement of Tumor Responses to Fractionated Irradiation by SR 4233 (Tirapazamine) and by Nicotinamide with Carbogen" *Int. J. Radiat. Oncol. Biol. Phys.* 28(1):145–150 (1994).

Epstein et al., "Treatment of Locally Advanced Cancer of the Head and Neck With 5'–Iododeoxyuridine and Hyperfractionated Radiation Therapy: Measurement of Cell Labeling and Thymidine Replacement" *J. Natl. Cancer Inst.* 86(23):1775–1780 (1994).

Forastiere, A.A., "Randomized Trials of Induction Chemotherapy" *Hematol. Oncol. Clin. North Am.* 5(4):725–736 (1991).

Glicksman et al., "Concurrent CIS–Platinum and Radiation With or Without Surgery For Advanced Head and Neck Cancer" *Int. J. Radiat. Oncol. Biol. Phys.* 30(5):1043–1050 (1994).

Guéritte–Voegelein et al., "Chemical Studies of 10–Deacetyl Baccatin III. Hemisynthesis of Taxol Derivatives." *Tetrahedron Letters* 42(16):4451–4460 (1986).

Hall, E.J., "CROS Conference on Chemical Modification–Radiation and Cytotoxic Drugs" *Int. J. Radiat. Oncol. Bio. Phys.* 8:323–325 (1982).

Hall and Roizin–Towle, "Hypoxic Sensitizers: Radiobiological Studies at the Cellular Level" *Radiology* 117:453–457 (1975).

Hart and Ha, "The Ester Enoulate–Imine Condensation Route to β–Lactams" *Chem. Rev.* 89(7):1447–1465 (1989).

Horwitz et al., "Taxol: Mechanisms of Action and Resistance" *Ann. N.Y. Acad. Sci.* 466:733–744 (1986).

Kant et al., "A Chemoselective Approach to Functionalize the C–10 Position of 10–Deacetylbaccatin III. Synthesis and Biological Properties of Novel C–10 Taxol Analogues" *Tetrahedron Letters* 35(31):5543–5546 (1994).

Kim et al., "Clinical and Biological Studies of Estramustine Phosphate As a Novel Radiation Sensitizer" *Int. J. Radiation Oncology Biol. Phys.* 29(3):555–557 (1994).

Kingston et al., "The Chemistry of Taxol, A Clinically Useful Anticancer Agent" *J. Nat. Prod.* 53(1):1–12 (1990).

Kingston, D.G.I., "The Chemistry of Taxol" *Pharmac. Ther.* 52:1–34 (1991).

(List continued on next page.)

*Primary Examiner*—Gary E. Hollinden
*Assistant Examiner*—Michael G. Hartley
*Attorney, Agent, or Firm*—Stephen E. Reiter; Gray Cary Ware & Freidenrich LLP

[57] ABSTRACT

In accordance with the present invention, there are provided derivatives of chemotherapeutic agents (e.g., paclitaxel), which serve as bifunctional agents. Invention derivatives retain the antitumor activity of the parent compound, and, coupled with the electron affinic substituents thereon, produce compounds which show a strong capability for radiosensitizing tumor cells growing in vitro. It is expected that a single drug which combines the properties of a radiosensitizer with chemotherapeutic activity will offer significant advantages not only to patients, but also to radiotherapists seeking improved modes of treatment. The combination of antitumor properties with electron-affinic function produces novel radiosensitizers, a second generation of drugs which are more powerful to fight cancers. Bifunctional agents with the dual properties of tubulin assembly and electron affinity will make the compounds useful not only as radiosensitizers, but also as cytotoxins.

4 Claims, 7 Drawing Sheets

OTHER PUBLICATIONS

Kingston et al., "The Taxane Diterpenoids" *Prog. Chem. Org. Nat. Prod.* 61:1–206 (1993).

Kingston, D.G.I., "Taxol: the chemistry and structure–activity relationships of a novel anticancer agent" *Trends Biotechnol.* 12:222–227 (1994).

Kingston et al., "Synthesis of Taxol from Baccatin III via an Oxazoline Intermediate" *Tetrahedron Letters* 35(26):4483–4484 (1994).

Lee et al., "A Phase I/II Study of the Hypoxic Cell Sensitizer Misonidazole as an Adjunct to High Fractional Dose Radiotherapy in Patients with Unresectable Squamous Cell Carcinoma of the Head and Neck: A RTOG Randomized Study (#79–04)" *Int. Radiat. Oncol. Biol. Phys.* 16:465–470 (1989).

Liebmann et al., "Changes in Radiation Survival Curve Parameters in Human Tumor and Rodent Cells Exposed to Paclitaxel (Taxol)" *Int. J. Radiat. Oncol. Bio. Phys.* 29(3):559–564 (1994).

Lustig et al., "Phase I/II Study of Fluosol–DA and 100% Oxygen as an Adjuvant to Radiation in the Treatment of Advanced Squamous Cell Tumors of the Head and Neck" *Int. J. Radiat. Oncol. Biol. Phys.* 16:1587–1593 (1989).

Mellado et al., "Preparation and Biological Activity of Taxol Acetates" *Biochem. Biophys. Res. Commun.* 124(2):329–336 (1984).

Milas et al., "Enhancement of Tumor Radioresponse of a Murine Mammary Carcinoma by Paclitaxel" *Cancer Res.* 54:3506–3510 (1994).

Mitchell et al., "Hypoxic Mammalian Cell Radiosensitization by Nitric Oxide" *Cancer Res.* 53:5845–5848 (1993).

Nicolaou et al., "Chemistry and Biology of Taxol" *Angew. Chem. Int. Ed. Engl.* 33:15–44 (1994).

Ojima et al., "New and Efficient Approaches to the Semisynthesis of Taxol and its C–13 Side Chain Analogs by Means of β–Lactam Synthon Method" *Tetrahedron* 48(34):6985–7012 (1992).

Oya et al., "In Vivo Radiosensitization Efficacy of KU–2285 and Etanidazole at Clinically Relevant Low Radiation Doses" *Int. J. Radiat. Oncol. Biol. Phys.* 27(5):1113–1119 (1993).

Rowinsky and Donehower, "PACLITAXEL (TAXOL)" *New England J. of Med.* 332(15):1004–1014 (1995).

Saunders et al., "Continuous Hyperfractionated Accelerated Radiotherapy in Locally Advanced Carcinoma of the Head and Neck Region" *Int. J. Radiat. Oncol. Biol. Phys.* 17:1287–1293 (1989).

Schiff et al., "Promotion of microtubule assembly in vitro by taxol" *Nature* 277:665–667 (1979).

Sinclair, W.K., "Cyclic X–Ray Responses in Mammalian Cells in Vitro" *Radiat. Res.* 33:620–643 (1968).

Steren et al., "Radiosensitization by Taxol of a human ovarian cancer cell line" *Proc. AACR* 33:552 (1992).

Steren et al., "Taxol as a Radiation Sensitizer: A Flow Cytometric Study" *Gynecol. Oncol.* 50:89–93 (1993).

Stratford, I.J., "Mechanisms of Hypoxic Cell Radiosensitization and the Development of New Sensitizers" *Int. J. Radiat. Oncol. Biol. Phys.* 8:391–398 (1982).

Suit and Miralbell, "Potential Impact of Improvements in Radiation Therapy of Quality of Life and Survival" *Int. J. Radiat. Oncol. Bio. Phys.* 16(4):891–895 (1989).

Thomas et al., "Correlation between Radiosensitivity, Percentage Hypoxic Cells and $pO_2$ Measurements in One Rodent and Two Human Tumor Xenografts" *Radiat. Res.* 139:1–8 (1994).

Thomlinson and Gray, "The Histological Structure of Some Human Lung Cancers and the Possible Implications for Radiotherapy" *British J. Cancer* 9(4):539–549 (1955).

Tishler et al., "Taxol Sensitizes Human Astrocytoma Cells to Radiation" *Cancer Res.* 52:3495–3497 (1992).

Tishler et al., "Taxol: A Novel Radiation Sensitizer" *Int. J. Radiat. Oncol. Biol. Phys.* 22:613–617 (1992).

Urtasun et al., "Binding of $^3$H–Misonidazole to Solid Human Tumors as a Measure of Tumor Hypoxia" *Int. J. Radiat. Oncol. Biol. Phys.* 12:1263–1267 (1986).

Vokes et al., "A Randomized Study Comparing Two Regimens of Neoadjuvant and Adjuvant Chemotherapy in Multimodal Therapy for Locally Advanced Head and Neck Cancer" *Cancer* 66(2):206–213 (1990).

Vokes et al., "Favorable Long–Term Survival Following Induction Chemotherapy With Cisplatin, Fluorouracil, and Leucovorin and Concomitant Chemoradiotherapy for Locally Advanced Head and Neck Cancer" *J. Natl. Cancer Inst.* 84(11):877–882 (1992).

Weissberg et al., "Randomized Clinical Trial of Mitomycin C as an Adjunct to Radiotherapy in Head and Neck Cancer" *Int. J. Radiat. Oncol. Biol. Phys.* 17:3–9 (1989).

Zhao and Kingston, "Modified Taxols, 6. Preparation of Water–Soluble Prodrugs of Taxol" *J. Nat. Prod.* 54(6):1607–1611 (1991).

Taxol

Taxol Derivative

Taxane Derivative

Scheme 1

Scheme 2

Scheme 3

Scheme 4

Scheme 5

Scheme 6

Scheme 7

NITROPHENYL, 10-DEACETYLATED SUBSTITUTED TAXOL DERIVATIVES AS DUAL FUNCTIONAL CYTOTOXIC/ RADIOSENSITIZERS

FIELD OF THE INVENTION

The present invention relates to the modification of antitumor drugs, such as paclitaxel, to impart radiosensitizing properties as well as chemotherapeutic properties thereto.

BACKGROUND OF THE INVENTION

Cancer is a dread disease that strikes at any age. Currently, radiotherapy and chemotherapy are two important methods employed for the treatment of cancer. Radiotherapy can often eradicate primary or localized disease; and chemotherapy may control or eliminate metastatic disease. The combination of radiotherapy with chemotherapy, so-called "adjuvant therapy", is aimed not only at producing higher tumor cell killing (by causing tumor shrinkage), but also at providing spatial cooperation, where the strong local effects of radiation therapy are complemented by systemic drug-induced cell death at micrometastatic sites in distant organs. Therefore, adjuvant therapy can increase survival rates for a number of solid tumors that were formerly treated by only one therapeutic modality.

According to data from the American Cancer Society, at least about 50–60% of cancer patients in the United States receive radiation therapy each year. However, current radiation treatment strategies still show a high rate of failure (Suit, H. D., Miralbeau, R., Int. J. Radiat. Oncol. Bio. Phy. 1989, 16:891–895).

It is currently believed that many solid tumors contain areas of diminished oxygen supply. Hypoxic cells, which are present in almost all tumor tissues, represent a problem in radiotherapy treatment of cancer, as these cells respond poorly to radiotherapy and to chemotherapy. Some investigators have proposed that hypoxia on tumor tissue results from two categories: diffusion limited (chronic hypoxia) and perfusion limited (acute hypoxia) (Thomlinson, R. H., Gray, L. H., Br. J. Cancer 1955, 9:539–549, Brown, J. M., Br. J. Cancer 1979, 52:650–656). Hall indicated that the radiation dose must be raised by a factor as great as 3 to achieve, in a totally hypoxic cell, the effect obtained in a fully oxic one. Indeed, it was discovered in the laboratory that the presence of 2–3% of such resistant cells may double the total radiation dose required for eradication of all tumor cells (Hall, E. J. Int. J. Radiat. Oncol. Bio. Phy. 1982, 8:323–325).

Considerable efforts have been made to develop methods to overcome the resistance of tumor cells to radiation. The use of the hyperbaric oxygen chamber was the first widely used approach in efforts to overcome the resistance caused by hypoxic tumor cells (Thomas, C. D., Chavaudra, N., Martin, L., Guichard, M., Radiat. Res. 1994, 139:1–8.; Churchill-Davidson, I., Sanger, C.; Thomlinson, R. H., Lancet. 1955,i 1091–1095). Other strategies have included the use of perfluorochemical emulsions combined with oxygen breathing, (Lustig, R., McIntosh, L. N., Rosem, C., Hass, J., Krasnow, C.; Spaulding, M., Prosnitz, L. Int. J. Radiat. Oncol. Biol. Phys. 1989 16, 1587–1593.), high linear energy transfer (LET) radiation, and hypoxic cell sensitizers to increase the amount and alter the quality of initial DNA and chromosome damage during radiation therapy.

Among these strategies, however, the more promising and easier method involves the combined use of chemicals that can selectively sensitize hypoxic cells to conventional low-LET radiation without effect on normal oxic cells. Adams and colleagues reported that 'electron affinic' compounds sensitize hypoxic cells as oxygen does (Adams, G. E. and Cooke, M. S. Int. J. Radiat. Biol:. 1969, 15:457–471). These authors speculated that there is a close relationship between electron affinity and potency of a compound as a hypoxic-cell sensitizer.

For the last two decades, the development of hypoxic-cell radiosensitizers has been given considerable attention. Several structural classes of compounds have been designed and synthesized as radiosensitizers. These include a variety of fused ring benzoquinones, organic N-oxides of different structures, various nitrobenzenes and nitroheterocyclics. Among them, nitroimidazole derivatives are considered to be one of the most effective radiosensitizers for hypoxic cells. Examples of such compounds include misonidazole, etamidazole, pimonidazole, RSU-1069 and RB-6145 (Hall, E. J., and Roizin-Towle, L. Radiology 1975, 117, 453–457; Stratford, I. J. Int. J. Radiat. Oncol. Biol. Phys. 1982, 8:391–398). Among these, misonidazole was found to be an excellent hypoxic-cell sensitizer in cultured mammalian cells and in some rodent tumors. Misonidazole has also been evaluated in systematic large-scale clinical trials, however, clinic application was not feasible because the drug proved to be toxic to the central nervous system.

Substantial long-term benefits have been reported in patients treated with nitroimidazole derivatives in combination with radiotherapy for advanced pharyngeal tumors (Overgaad, J., Sand-Hansen, H., Lindelov, B., Overgaad, M., Jorgensen, K., Rasmusson, B., and Berthelsen, A., Radiother. Oncol. 1991, 20, Suppl. 1:143–149). In general, nitroimidazoles, which act as hypoxic cell sensitizers and have a strong affinity for hypoxic cells, have been shown to bind to cells in human tumors (Urtason, R.C., Chapman, L. H., Raleigh, J. A., Franko, A. J., Koch, C. J., Int. J. Radiat. Oncol. Biol. Phys. 1986, 12, 1263–1267).

A molecular mechanism of the role of nitro compounds in the radiosensitization of hypoxic cells has been proposed, which involves (1) an increase in the oxidative damage of DNA, to give hydroxy compounds under deoxygenated conditions, and (2) suppression of intracellular radio–protectors of sulfhydryl compounds. The oxidation of DNA and reaction with glutathione occur via electron transfer to nitro compounds. The mechanism of the electron migration model postulates long range intramolecular migration of electrons liberated by radiation along the DNA structure. The ability of sensitizers present in, or near to, the DNA to act as electron traps which can influence the distribution of free radical centers in the DNA, and consequently influence the extent of radiation damage to DNA (Adams, G. E. and Cooke, M. S. Int. J. Radiat. Biol. 1969, 15:457–471). In addition to the above proposed mechanism, direct reaction between the sensitizer molecule and free radical centers on DNA has also been proposed.

In the radiotherapeutic control of malignant tumors, it would be desirable to employ a hypoxic-cell radiosensitizer that is highly effective and minimally toxic. Ideal agents, which would be anaerobically reduced to a cytotoxin, should be more cytotoxic to hypoxic tumor cells than to oxygenated normal tissues. Many nitroheterocyclic compounds and nitrobenzenes owe their selective cytotoxicity toward hypoxic cells within tumors to their bioreductive properties. These compounds are activated in vivo by anaerobic, enzymatic reduction to form metabolites, such as aminoheterocyclics, which are considerably more cytotoxic than the parent compound from which they were derived.

Considerable efforts have been made to develop new compounds useful as radiosensitizers. For example, 5'-iododeoxyuridine (IdUrd), 5'-bromodeoxyuridine (BrdUrd) (Epstein, A. H., Lebovics, R. S., Goffman, T., Teague, D., Fuetsch, E., S., Glatstein, E., Okunieff, P., Cook, J. A., J. Natl. Cancer Inst. 1994, 86:1775–1780), 5-fluorouracil (Fura) (Lawrence, T. S.; Maybaum, J. Sam. Radiat. Oncol., 1993, 3:20–28), fluorinated 2-nitroimidazole (Oya, N., Shibamoto, Y., Sasai, K., Sugiyama, T., Abe, M., Int. J. Radiat. Oncol. Biol. Phys. 1993, 27(5):1113–1119), nitric oxide (Mitchell, J. M., Wink, D. A., DeGraff, W., Gamson, J., Keefer, L. K., Krishna, M. C. Cancer Res. 1993, 53:5845–5848), estramustine phosphate (Kim, J. H., Khil, M. S., Kim, S. H., Ryu, S., Gabel, M. Int. J. Radiat. Oncol. Biol. Phys. 1994, 29(3), 555–557) and benzotriazine di-N-oxides (tirapazamine) (Dorie, M. J., Menke, D., Brown, J. M., Int. J. Radiat. Oncol. Biol. Phys. 1994, 28(1), 145–149) are under active study as radiation sensitizers for a variety of malignancies. Benzotriazine di-N-oxides (tirapazamine) are presently in Phase I clinical testing, representing the first drug to be introduced to the clinic as an agent specifically toxic to hypoxic cells.

A variety of new treatment strategies have been proposed to reduce local failure after radiotherapy. Protocols involving radical curative surgery with radiation, hyperfractionated radiation (Sauders, M. I., Dische, S., Hong, A., Grosch, E. J., Fermont, D. C., Ashford, R. F., Maher, E. J., Int. J. Radiat. Oncol. Biol. Phys. 1989, 17:1287–1293; Glicksman, A. S., Slotman, G., Doolittle, C. Clark, J., Koness, J., Coachman, N., Posner, M., DeRosa, E., Wanebo, H., Int. J. Radiat. Oncol. Biol. Phys. 1994, 30(5):1043–1050), neoadjuvant chemotherapy (Forastiere, A. A. Hematol. Oncol. Clin. North Am., 1991, 5(4):725–736), and sequential combinations of chemotherapy, surgery, and radiation (Vokes, E. E., Panje, W. R., Mick, R., Kozloff, M. F., Moran, W. J., Sutton, H. G., Goldman, M. D., Tylbor, A. G., Weichselbaum, A. A. Cancer 1990, 66(2):206–213) have frequently been used. The approach utilizing chemotherapy as the first-line treatment, followed by surgery or radiation therapy, has been developed. Thus, the primary tumor can be shrunk before local eradication is attempted, and micrometastatic foci can be initially attacked, without waiting until local treatment is completed. In all of these protocols, there is an urgent need of effective radiosensitizers.

A greater cell killing effect can be obtained by use of a combination of radiotherapy with certain drugs which can enhance the cell killing effects of radiation in tumor cells. During the last decade, the synergistic effects of simultaneously administered chemotherapy and radiation in cancer has been recognized, employing a variety of chemotherapeutics, including misonidazole (Lee, D. J.; Pajak, T. F., Stetz, J., Order, S. F., Weissberg, J. B., Fischer, J. J. Int. J. Radiat. Oncol. Biol. Phys. 1989, 16:465–470), mitomycin-C (Weissberg, J. B., Son, Y. H., Papac, R. J., Saski, C. Fischer, D. B., Lawrence, R., Rochwell, S., Sartorelli, A. C., Fischer, J. J. Int. J. Radiat. Oncol. Biol. Phys. 1989, 17:3–9), cis-platinum (Crissman, J. D., Pajak, T. F., Zarbo, R. J., Marcial, V. A., Al-Sarraf, M., Cancer, 1987, 58(8), 1391–1397), cis-platinum plus 5-fluorouracil (Vokes, E. E., Weichselbaum, R. R., Mick, R. McEvilly, J. M., Haraf, D. J., Panje, W. R., J. Natl. Cancer Inst. 1992, 84(11):877–82).

Although radiobiologists and radiotherapists have evaluated many rediosensitizers, such as hyperbaric oxygen, nitroimidazole, halogenated pyrimidine, cis-platin, both experimentally and clinically, thus far, results from clinical trials using these approaches have not been particularly successful. Therefore, new compounds designed to improve the success rate of conventional radiation therapy are urgently needed and have an enormous potential for cancer therapy.

Paclitaxel (taxol, see FIG. I, structure I), a naturally occurring diterpenoid isolated from the bark of the western yew Taxus brevifolia, has shown an excellent and broad spectrum of antileukemic and tumor-inhibiting activity. Indeed, this compound is currently being developed and is considered as one of the most exciting leads for antitumor drugs. Paclitaxel has already been approved for use in the palliative therapy of patients with ovarian and breast cancers resistant to chemotherapy and is currently in clinical trial for various other types of cancers, such as lung, head and neck cancer (for review see: a) Rowisky, E. K., Donehower, R. C. New England J. of Med. 1995, 332 (15):1004–1014, b) Kingston, D. G. I. Samaranayake, G.; Ivey, C.A. J Nat. Prod., 1990 53:1–12, c) Blechert, S.; Gu nard, D. In The Alkaloids, Chemistry and Pharmacology; Brossi, A. Ed.; Academic Press: San Diego, 1990; Vol. 39, pp 195–238, d) Kingston, D. G. I. Pharmac. Ther. 1991, 52:1–34, e) Kingston, D. G. I.; Molinero, A. A.; Rimoldi, J. M. Prog. Chem. Org. Nat. Prod. 1993, 61:1–188, f) Kingston, D. G. I. Trends Biotechnol. 1994, 12:222–227). Studies have also revealed that paclitaxel is a potent in vivo radiopotentiating agent and has the potential to be usefully combined with radiotherapy. (Milas, L., Hunter, N. R., Mason, K. A., Kurdoglu, B., Perters, L. J., Cancer Res. 1994, 54:3506–3510).

Paclitaxel inhibits cell replication in the mitotic phase of the cell cycle by promoting polymerization and stablization of microtubules. Microtubules are polymers of tubulin in dynamic equilibrium with tubulin heterodimers, composed of alpha and beta protein subunits. Generally, microtubules are believed to function primarily as the major constituent of the mitotic spindle apparatus. However, microtubules are also required by the cell for performance of many vital interphase functions, including maintenance of shape, motility, anchorage, mediation of signals between cell surface receptors and the nucleus, and intracellular transport, especially in neural and secretory cells.

Unlike other antimicrotubule agents, such as the vinca alkaloids (which induce microtubule disassembly), paclitaxel shifts the equilibrium towards microtubule assembly. Paclitaxel-induced microtubules are excessively stable, thereby inhibiting the dynamic reorganization of the microtubule network. Its cytotoxic properties are caused by its unique disruptive effects on microtubules. These microtubular changes affect cells mostly in G2 and M phase, and prevent completion of cell division, which in turn results in the accumulation of cells in G2/M phase (Schiff, P. B., Fant, J., and Horwitz, S. B., Nature 1979, 22:665–667, b) Horwitz, S. B., Othstein, L., Manfredi, J. J. Mellado, W., Parness, J. Roy, S. N., Schiff, P. B. Sorbara, L., and Zeheb, R. Ann. N.Y. Acad. Sci. 1986, 466:733–744). This perturbation of the cell cycle probably results from the inability of these cells to form a normal mitotic spindle after treatment, and progression through mitosis is halted. The ability of paclitaxel to arrest cells in the G2/M phase opens up the possibility of its use as a radiosensitizer, because the G2/M phase is the most radio sensitive phase of the cell cycle (Sinclair, W. K. Radiat, Res. 1968, 33:620–643). On the basis of this analysis, it is believed that paclitaxel shows promise both as a chemotherapeutic agent and as a possible adjunct to radiation therapy.

Recently, paclitaxel was examined as a potential radiosensitizing agent using the grade III human astrocytoma cell line, G18. The results of this study demonstrated that a combination of paclitaxel pretreatment and gamma irradiation produced a significant enhancement of radiosensitivity, which was dependent upon both the drug dose and time of treatment with paclitaxel (Milas, L. Hunter, N. R. Msdon, K., A., Kurdoglu, B. Peters, L. Cancer Res. 1994, 54:3506–3510; Tishler, R. B., Geard, C. R., Hall, E. J., Schiff, P. B., Cancer Res. 1992, 52:3495–3497; Tishler, R. B., Schiff, P. B, Geard, C. R., Hall, E. J., Int. J. Radiat. Oncol. Biol. Phys. 1992, 22:613–617). The radiosensitization of HL-60 human leukemic cell line, G-18 astrocytoma cell line and three human ovarian cancer cell lines by paclitaxel has been also disclosed (a) Tishler, R. B., Schiff, P. B., Geard, C. R. and Hall, E. J. Int. J. Radiat. Oncol. Bio. Phys. 1992:613–617; b) Steren, A., Sevin, B. U., Perras, J. P., Angioli, R., Nguyen, H. N., Guerra, L., and Averette, H. E., Proc. AACR , 1992, 33:552; c) Steren, A., Sevin, B.-U., Perras, J., Ramos, R., Angioli, R., Nguyen, H.; Koechli, O., and Averette, H. E. Gynecol. Oncol. 1993, 50:89–93).

Investigators, however, have not observed an enhancement in radiosensitization by paclitaxel in cervical carcinoma cell lines (Minarik, L., Hall, E. H. Radiotheraphy and Oncology, 1994, 32:124–128) or human breast and lung cell lines (Liebmann, J., Cook, J. A., Fisher, J., Teague, D., Mitchell, J. B. Int. J. Radiat. Oncol. Bio. Phys, 1994, 29(3):559–564). The degree of radiosensitization observed is modest and is comparable to that seen with other chemotherapeutic agents, including fluorouracil and cisplatin. Indeed, it has been questioned whether adequate protracted, continuous tissue concentrations of drug would be achievable for daily radiation treatments, in view of the fact that paclitaxel is currently administered to patients through intravenous infusion every 2–3 weeks (even considering that the serum half-life of paclitaxel is up to 19 h) (Kim, J. H., Khil, M. S., Kim, S. H., Ryu, S., Gabel, M. Int. J. Radiation Oncology Biol. Phys. 1994, 29(3):555–557). Thus, although paclitaxel is a promising anticancer chemotherapeutic agent and has also demonstrated some potential as a radiosensitizer, these data indicate that the use of paclitaxel as a radiosensitizer is limited.

The possibility of using chemotherapeutic agents to selectively enhance radiation response in tumors is an appealing approach to improving the results of cancer treatment. Besides augmenting the cytotoxic action of radiation, combined modality treatment offers the prospect of spatial cooperation, whereby the powerful local effect of precisely directed radiation therapy on gross tumor deposits is complemented by the systemic effect of drugs on micrometastatic disease. The ideal drug for this therapeutic strategy would have potent independent anticancer action, as well as the ability to sensitize radioresistant tumor cells to the lethal effects of ionizing radiation.

BRIEF DESCRIPTION OF THE INVENTION

In accordance with the present invention, we have developed derivatives of chemotherapeutic agents (e.g., paclitaxel), which serve as bifunctional agents. Invention derivatives meet each of the above requirements, because the antitumor activity of the parent compound, coupled with the electron affinic substituents thereon produce compounds which show a strong capability for radiosensitizing tumor cells growing in vitro. It is expected that a single drug which combines the properties of a radiosensitizer with chemotherapeutic activity will offer significant advantages not only to patients, but also to radiotherapists seeking improved modes of treatment.

The combination of antitumor properties with electron-affinic function produces novel radiosensitizers, a second generation of drugs which are more powerful to fight cancers. Bifunctional agents with the dual properties of tubulin assembly and electron affinity will make the compounds useful not only as radiosensitizers, but also as cytotoxins.

In accordance with the present invention, 'electron affinic' group(s) are attached to a chemotherapeutic (e.g., paclitaxel). It is expected that the resulting bifunctional derivatives will function as both cytotoxin and radiosensitizing agent. The aim of combining local radiotherapy with systemic chemotherapy is to increase the therapeutic index when treating malignant tumors. In one aspect, these derivatives work as radiosensitizers by positioning the oxygen mimetic species near the target of radiation, DNA; in another aspect, these derivatives can serve as hypoxic cytotoxins by conferring on the chemotherapeutic moiety, which itself has potent anti-tumor activity, an increased selective toxicity in hypoxic cells (by virtue of the attached electron affinic functionalities). Invention compounds demonstrate the possibility that 'electron affinic' agents, such as nitroimidazoles and nitroaromatics, when attached to a chemotherapeutic compound, result in chemicals that are useful in chemotherapy and radiotherapy.

In recent years, the clinical importance of paclitaxel has promoted the synthesis of novel analogues with the goal of designing more effective chemotherapeutic agents. Several total syntheses and semi-syntheses of paclitaxel and its analogues have been disclosed in the prior art. In addition, structure-activity correlations for paclitaxel analogues have been established (for review see: (a)Kingston, D. G., Pharmac. Ther. 1991, 52:1–34; b) Nicolaou, K. C., Dai, W.–M., Guy, R. K. Angew. Chem. Int. Ed. Engl., 1994, 33:15). In accordance with the present invention, novel syntheses for the preparation of paclitaxel derivatives are provided. The present approach to synthesis of invention compounds offers the combined advantages of good preparative yield, a minimum number of reaction steps, and synthetic flexibility in the design of derivatives of paclitaxel.

The novel paclitaxel derivatives in general have the structural formula set forth in FIG. 1, as structure II. In the FIG., $R_1$ is selected from hydrogen, alkyl, alkenyl, alkynyl, aryl, or heteroaryl, a protected hydroxy group, or a functional group which increase the water solubility of the taxane;

$R_2$ is selected from hydrogen, alkyl, alkenyl, alkynyl, aryl, heteroaryl, heterosubstituted alkyl, alkenyl, alkynyl, aryl, heteroaryl, nitroaryl or nitroheterocyclyl;

$R_3$ is selected from —$COR_6$, —$COOR_6$, —$COSR_6$, $CONR_7R_8$, or —$SO_2R_9$;

$R_4$ and $R_5$ are each independently selected from —$COR_6$, —$COOR_6$, —$COSR_6$, $CONR_7R_8$, or —$SO_2R_9$;

$R_6$ is selected from alkyl, alkenyl, alkynyl, aryl, acyl, heteroaryl, heterosubstituted alkyl, alkenyl, alkynyl, aryl, heteroaryl, nitroaryl or nitroheterocyclyl;

$R_7$ is selected from hydrogen, alkyl, alkenyl, alkynyl, aryl, acyl, heteroaryl, heterosubstituted alkyl, alkenyl, alkynyl, aryl, heteroaryl, nitroaryl or nitroheterocyclyl;

$R_8$ is selected from hydrogen, alkyl, alkenyl, alkynyl, aryl, acyl, heteroaryl, heterosubstituted alkyl, alkenyl, alkynyl, aryl, heteroaryl, nitroaryl or nitroheterocyclyl; and $R_9$ is selected from alkyl, alkenyl, alkynyl, aryl, acyl, heteroaryl, heterosubstituted alkyl, alkenyl, alkynyl, aryl, heteroaryl, nitroaryl or nitroheterocyclyl.

DETAILED DESCRIPTION OF THE INVENTION

Figure 1:
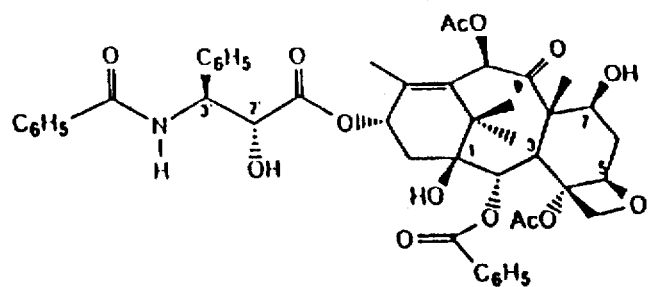
FIG. 1 presents the structure of taxol, a novel derivative thereof according to the present invention, as well as the structure of a taxane derivative.
Figure 1:
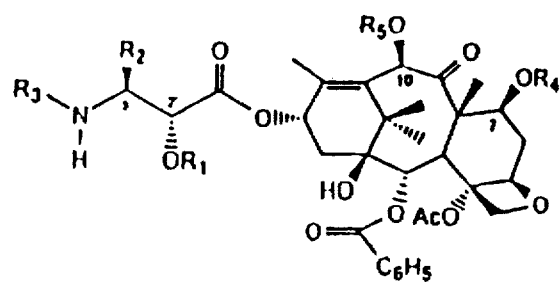
Figure 1:
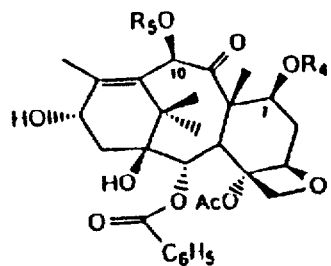

In accordance with the present invention, there are provided dual functional compounds having both cytotoxic properties and radiosensitizing properties. Invention compounds comprise modified cytotoxic agents having one or more electron affinic groups thereon.

Electron affinic groups can be introduced into invention compounds at a variety of reactive sites within the cytotoxic agent. Preferred modified cytotoxic agents according to the invention comprise a cytotoxic agent having chemically attached to a reactive site thereon at least one electron affinic group, wherein the site of attachment is selected so as to minimize the impact of the electron affinic group on the cytotoxic properties of the cytotoxic agent.

Those of skill in the art can readily identify numerous electron affinic groups which can be employed in the practice of the present invention. Exemplary electron affinic groups include nitroimidazoles, nitroaromatics, nitroheterocycles, carbonylaromatics, fused ring benzoquinones, organic N-oxides, sulfonyl aromatics, aromatic nitriles, and the like. Presently preferred electron affinic groups for use in the practice of the present invention include nitrofuranyl, nitrothionyl, 2-nitroimidazole, 4-nitroimidazole, 5-nitroimidazole, nitrophenyl and N-oxides.

Those of skill in the art can readily identify numerous cytotoxic agents which can be modified in accordance with the present invention. Exemplary cytotoxic agents include taxol and derivatives thereof, 5-fluorouracil, 5-fluoro-2'-deoxyuridine, cisplatin, carboplatin, methotrexate, 6-mercaptopurine, 6-thioguanine, hydroxyurea, 2-chlorodeoxyadenosine, cytarabine, melphalan, chlorambucil, mitomycin, streptozocin, anthracyclines, fludarabine, pentostatin, tiazofurin, ribavirin, mithramycin, azacytidine, mitoxantrone, dactinomycin, bleomycin, vinca alkaloids, glucocorticoids, teniposide, and the like. Presently preferred cytotoxic agents for use in the practice of the present invention include taxol and derivatives thereof, 5-fluorouracil, 5-fluoro-2'-deoxyuridine, cisplatin and 6-mercaptopurine.

In the preparation of derivatives of therapeutic agents bearing electron affinic groups (e.g., paclitaxel), two questions needed to be addressed: selection of the electron affinic group(s), and the selection of the site of attachment to the therapeutic agent. The linkage of electron affinic functionality(ies) to the skeleton of therapeutic agents (e.g., taxanoids) will produce new analogues with promise as dual function agents, i.e., having the properties of both antitumor agents and potent radiosensitizers.

Nitroaromatic or nitroheterocyclic moieties were selected as the initial electron affinic groups for synthetic work described herein. The position of attachment of the electron affinic group to paclitaxel was first chosen as the C-7 position, since earlier work showed that paclitaxel analogues carrying acetyl at C-7 retain most of the activity of paclitaxel.

Inspection of the structure of paclitaxel reveals that among the free hydroxyl groups in paclitaxel, the 1-hydroxy group is tertiary (and thus substantially nonreactive), the 7-hydroxyl group is relatively crowded, and the 2'-hydroxyl group is the most reactive. Thus, acylation of the 2'-hydroxyl group resulted in synthesis of paclitaxel analogues with enhanced water-solubility (Zhao, Z., Kingston, D. G. I. J. Nat. Prod. 1991, 54:1607–1611).

Although a series of functional groups can be introduced at the 2'-hydroxyl group, a substantial decrease of cytotoxicity has been observed. By comparison, C-7 substituted paclitaxel analogues have been observed to retain their biological activities. For instance, an acetyl at the 2'-position resulted in a loss in the ability to promote microtubule assembly, while acylation at C-7 does not significantly reduce this activity of paclitaxel. Mellado et al. observed that attachment of a polar sugar residue at C-7 slightly increases the microtubule assembly activity (Mellado, W., Magri, N. F., Kingston, D. G. I. Garcia-Arenas, R.; Orr, G. A., Horwitz, S. B.; Biochem. Biophys. Res. Commun. 1984, 124:329). Thus, in one aspect of the present invention, attachment of electron affinic group(s) at C-7 are expected to retain the cytotoxic activity of paclitaxel, and, in addition, to demonstrate activity as a radiosensitizer.

In order to introduce electron affinic group(s) at the 7-position, blocking of the 2'-hydroxyl group is required. The use of selective protecting groups are preferred. An excellent protecting group is the triethylsilyl group, because it is easily removed from the 2'-position by treatment with hydrofluoric acid in pyridine (or hydrochloric acid in methanol). 2,2,2-Trichloroethyl-oxycarbonyl derivatives can also be used, as this protecting group can be selectively removed by treatment with zinc and acetic acid.

Figure 2:
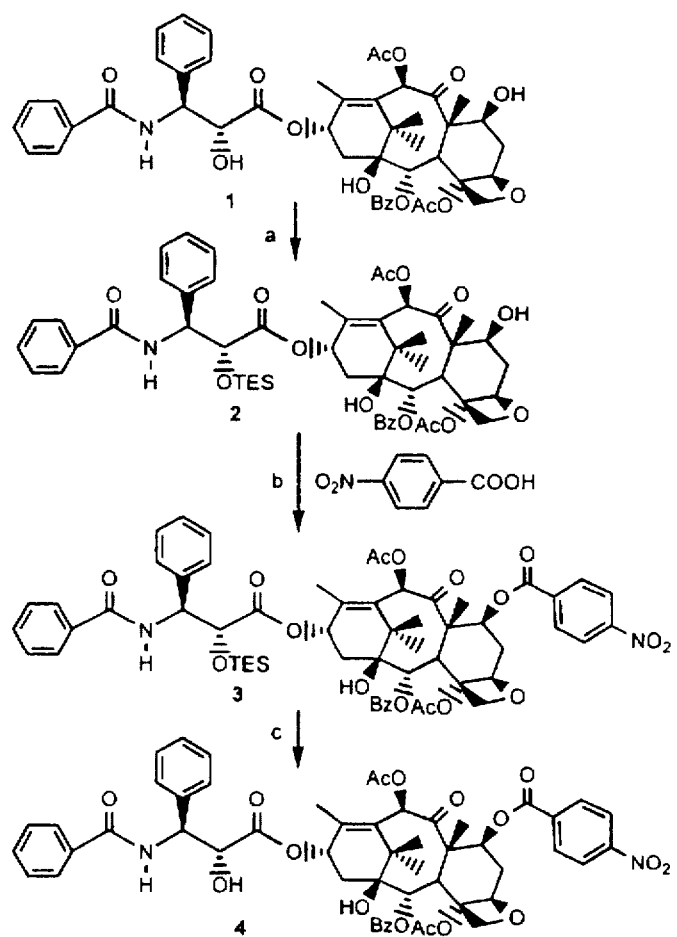
FIG. 2 presents a synthetic scheme (Scheme 1) for the preparation of 7-substituted taxol derivatives. In the scheme, conversion "a" employs a combination of chlorotriethylsilane (TESCl), pyridine and $CH_2Cl_2$; conversion "b" employs DCC, DMAP and $CH_2Cl_2$; and conversion "c" employs HF and pyridine.

Scheme 1 (see FIG. 2) shows an example of such a transformation. Thus, upon treatment of paclitaxel with chlorotriethylsilane (TESCl), in the presence of a base, such as pyridine, 2'-triethylsilyl paclitaxel 2 was afforded in high yield. When 2'-triethylsilyl paclitaxel was subjected to 4-nitrobenzoic acid, in the presence of dicyclohexylcarbodiimide and a catalytic amount of 4-pyrrolidinopyridine or 4-dimethylaminopyridine (step b of Scheme 1), the 7-acylation product 3 was obtained, from which the 2'-triethylsilyl group can readily be removed under mild acidic conditions (step c).

Alternatively, esterification at the C-7 position of 2'-protected paclitaxel 2 could be accomplished by use of an acid chloride. Treatment of 2'-protected paclitaxel with acid chloride bearing one or more nitro groups (such as nitroaromatics and nitroheteryclics) in the presence of a base, such as pyridine and/or triethylamine, will give the same 7-acylation products as 4 (see Scheme 1, FIG. 2).

Figure 3:
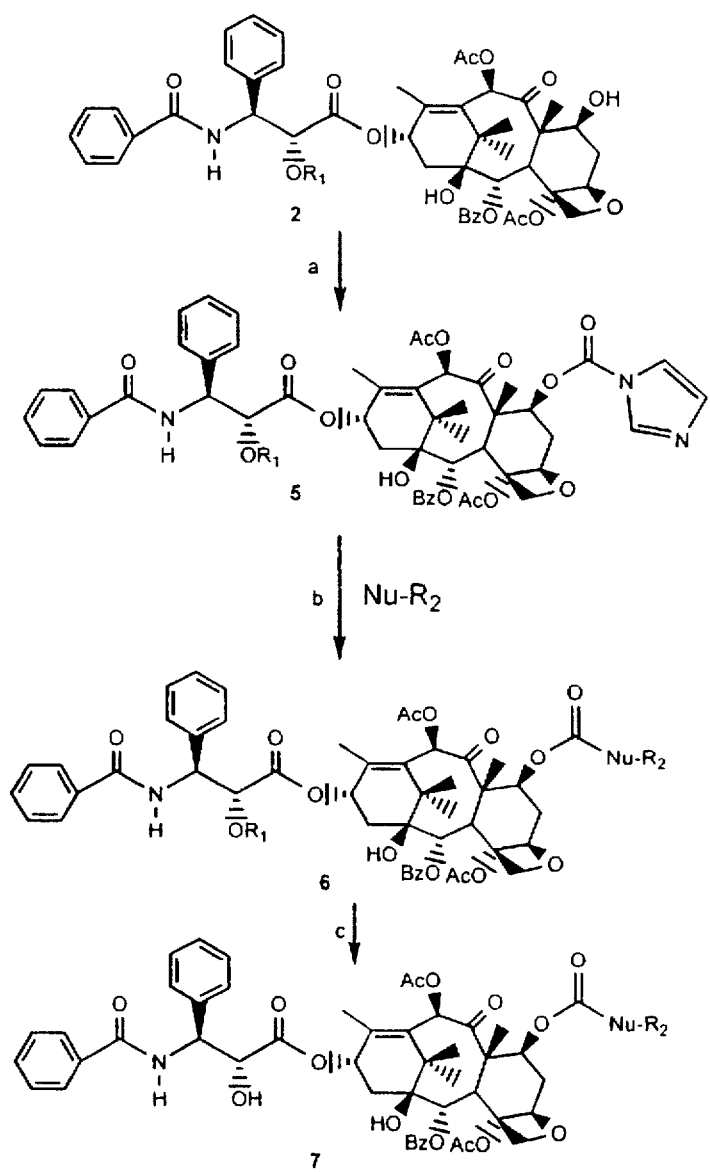
FIG. 3 presents an alternate synthetic scheme (Scheme 2) for the preparation of 7-substituted taxol derivatives. In the scheme, conversion "a" employs a combination of 1,1-carbonyldiimidazole (CDI) and $CH_2Cl_2$; conversion "b" employs $CH_2Cl_2$ as solvent for the nucleophilic species, $Nu-R_2$; and conversion "c" employs HF and pyridine.

With the availability of 2'-protected paclitaxel, further modification at the 7-position can be accomplished by using different linkages between the electron affinic group(s) and taxanes. Such linkages can be carbonate, carbamate, and the like. Thus, treatment of 2'-protected paclitaxel with 1,1-carbonyldiimidazole (CDI) in dichloromethane at room temperature affords the 2'-protected 7-(carbonylimidazole)-paclitaxel 5 (see Scheme 2, FIG. 3). Reaction of a nucleophile bearing one or more nitro groups on the aromatic or heterocyclic ring, such as an alcohol or an amine, leads to the formation of carbonate or carbamate linkaged paclitaxel analogues 6 (see Scheme 2, FIG. 3). Deprotection of 6 by standard methods will provide the 7-nitroimidazole-paclitaxel 7. In this way a variety of 7-modified paclitaxel derivatives can be synthesized employing carbonate and/or carbamate linkages.

Another strategy for the synthesis of nitro paclitaxel derivatives is to first modify taxane and then attach a C-13 side chain thereto. Once attachment of an electron affinic group on the taxane skeleton is complete, the side chain can thereafter be introduced by a variety of published procedures. This strategy proves to be more flexible for the preparation of nitro paclitaxel analogues.

In general, taxane derivatives contemplated for use in the practice of the present invention have the general formula as set forth in FIG. 1. In the FIG., $R_4$ and $R_5$ are as previously defined.

10-Deacetyl baccatin III (10-DAB) is a relatively abundant taxane that can be extracted in high yield from the needles of taxus brevifolia, the English yew, a renewable resource. Moreover, the isolation of 10-DAB, a tetraol, is significantly simpler and more economical than the isolation of paclitaxel, due to its polarity and high degree of crystallinity. Therefore, 10-DAB is a desirable starting material for the preparation of modified taxanes having electron affinic groups.

Potier et al. describe the acetylation of 10-DAB with acetic anhydride, reporting that no selectivity was seen between the C-7 and C-10 hydroxyl groups, and that the C-13 hydroxyl group is the least reactive (Gueritte-Voegelein, F., Senilh, V., David, B., Guenard, D., Potier, P. Tetrahedron, 1986, 42:4451–4460). It has been reported in the art, however, that under carefully controlled conditions, the selective protection of the 7-hydroxyl and 10-hydroxyl groups is possible (Denis, J.-N., Greene, A. E., Gu nard, D., Gu ritte-Voegelein, F., Mangatal, L., Potier, P. J. Am. Chem. Soc. 1988, 110:5917).

Figure 4:
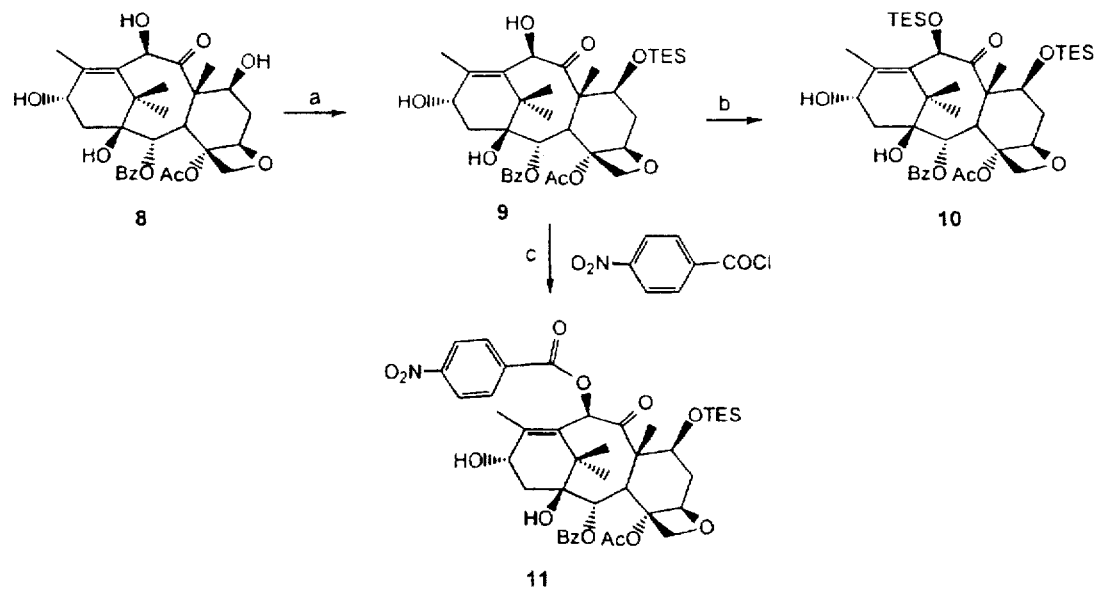
FIG. 4 presents a synthetic scheme (Scheme 3) for the preparation of derivatives of 10-deacetyl baccatin III (10-DAB). In the scheme, conversion "a" employs a combination of TESCl and pyridine; conversion "b" employs nBuLi, TESCl and THF; and conversion "c" employs nBuLi in THF.

Thus, treatment of 10-DAB with chlorotriethylsilane in pyridine gives 7-triethylsilyl 10-DAB (9 in Scheme 3, see FIG. 4). Given the availability of 7-triethylsilyl 10-DAB, further modification of C-10 hydroxyl group can be investigated. For instance, 7-triethylsilyl 10-DAB may be selectively acylated by acetyl anhydride in pyridine to give 7-triethylsilyl baccatin III.

Structure and activity relationship studies have disclosed that removal of the C-10 acetyl group of paclitaxel slightly reduces the tubulin disassembly activity and cytotoxicity. However, docetaxel (taxotere, 10-deacetylpaclitaxel derivative) is actually more active than paclitaxel in microtububle assembly activity and cytotoxicity. Kant et al. found that modification at the C-10 position of paclitaxel potentially results in higher antitumor activity (Kant, J., O'keeffe, W. S., Chen, S.-H., Farina, V., Fairchild, C., Johnston, K., Kadow, J. F., Long, B. H., and Vyas, D. Tetrahedron Letter, 1994, 35(31):5543–5546). These observations suggest that the 10-position, like the 7-position, is a suitable site for the attachment of electron affinic groups.

7-Protected 10-DAB can be selectively deprotonated at the C-10 hydroxyl, since the C-13 hydroxyl group is sterically congested, in addition to the possibility of hydrogen bonding between the C-13 hydroxyl group and the C-4 acetate moiety. The 10-hydroxyl group in 7-protected 10-DAB may be selectively deprotonated by a base, such as alkyllithium or sodium hydride, then subjected to a variety of electrophiles, such as alkyl halides, acyl halides, alkyl or phenyl chloroformates, alkylisocyanates, alkylcarbamyl chlorides, alkysulfonyl chlorides, and the like, to afford a series of derivatives of 10-DAB which can used for reaction with a side chain precursor to prepare paclitaxel derivatives. In this way a variety of functionalities (esters, ethers, carbonates, carbamates, sulfonates, and the like) can be introduced at the C-10 position of taxane.

As illustrated in Scheme 3 (see FIG. 4), C-10 alkoxymetal anion can generated upon treatment with metal hydride and metal alkyl, such as n-butyllithium and lithium bis (trimethylsilyl)amide, in THF at low temperature. Treatment of this C-10 alkoxyanion generated from 9 with chlorotriethylsilane will provide the 7,10-bistriethylsilyl 10-DAB 10. Alternatively, trapping of the C-10 alkoxymetal anion with 4-nitrobenzoyl chloride affords the nitro derivative of 10-DAB 11, which can be a key intermediate for the preparation of nitro paclitaxel derivatives.

Attachment of an electron affinic group on 7-position of paclitaxel can be accomplished employing a similar strategy. Among the three hydroxyl groups in baccatin III, the 1-hydroxyl group is tertiary (and hence substantially inert) and the 13-hydroxyl group is sterically crowded. Thus, the 7-hydroxyl group is the most active. Therefore, the 7-hydroxyl group of baccatin III can be selectively activated by some agents, such as 1,1-carbonyldiimidazole, so the modification of baccatin III at the 7-position can be readily carried out.

Reaction of 7-activated baccatin III with a variety of nucleophiles, such as alcohol, amine or sulfur compounds, results in the formation of compounds that possess electron affinic group(s), which is joined by formate, urethane or thioformate linkages, respectively. This modification provides a series of compounds with electron affinic functionality(ies) on the 7-position of baccatin III.

Figure 5:
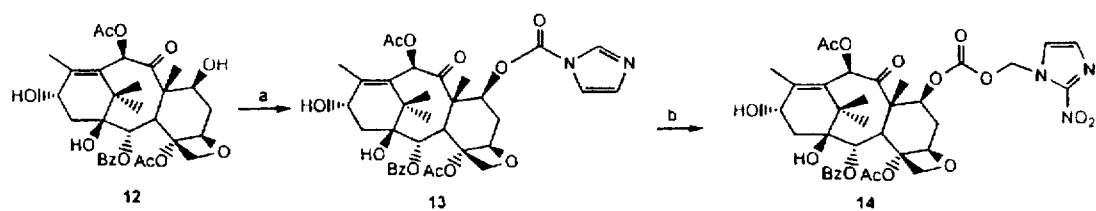
FIG. 5 presents an alternate synthetic scheme (Scheme 4) for the preparation of derivatives of baccatin III. In the scheme, conversion "a" employs a combination of CDI and $CH_2Cl_2$; and conversion "b" employs nitroimidazolemethanol and $CH_2Cl_2$.

As shown in Scheme 4 (see FIG. 5), baccatin III can be transformed into 7-carbonylimidazole baccatin III 13 by treatment with 1,1-carbonyldiimidazole in dichloromethane. Reaction of 7-carbonylimidazole baccatin III with 2-nitroimidazolemethanol in dichloromethane at room temperature produces the 7-substituted baccatin III 14 (see Scheme 4, FIG. 5), which can be used for the preparation of paclitaxel analogues by coupling with a C-13 side chain precursor.

Studies have indicated that the C-13 side chain is both the most investigated and the most critical part of paclitaxel for activity recognized to date. The potential semisynthesis of paclitaxel was first accomplished by Potier (Gueitte-Voegelein, F., Senilh, V.; David, B., Guenard, D., Potier, P. Tetrahedron, 1986, 42:4451.), who employed esterification of baccatin III derivatives with protected N-benzoyl-3-phenylisoerine to prepare paclitaxel. Since then, significant efforts have been made in a search for new acylating agents. N-Acyl-B-lactam (Holton, R., H., U.S. Pat. No. 5,175,315, 1992), oxazolines (Kingston, D. G. I., Chaudhary, A. G., Leslie Gunatilaka, A. A., Middleton, M. L., Tetrahedron Lett. 1994, 35(26):4483–3384) have been disclosed as potent acylating agents for the synthesis of paclitaxel.

Figure 6:
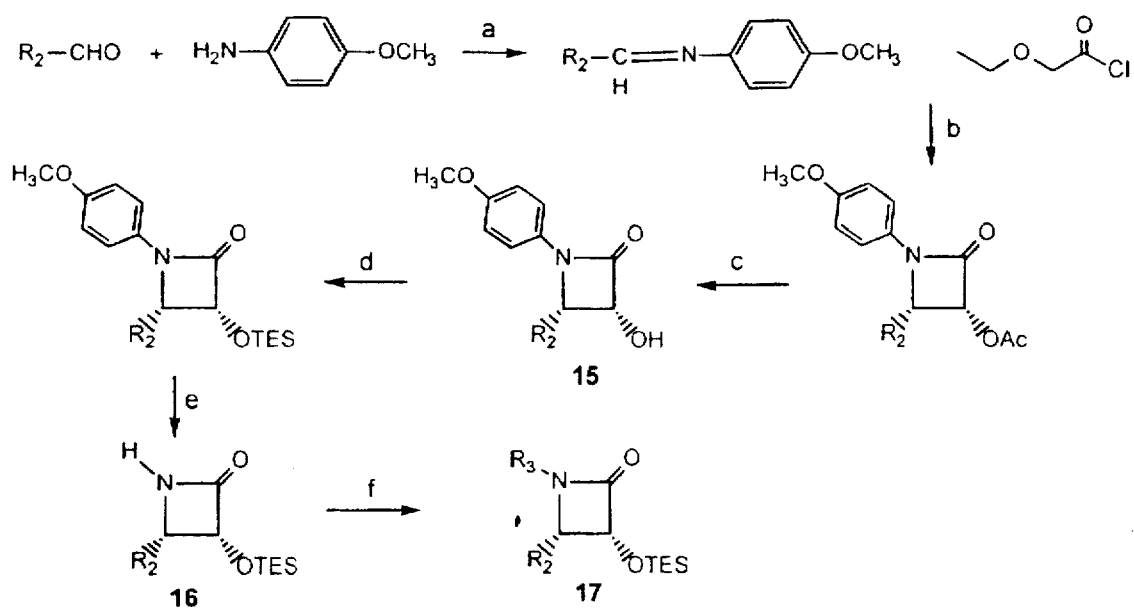
FIG. 6 presents a synthetic scheme (Scheme 5) for the preparation of β-lactams. In the scheme, conversion "a" is carried out in $CH_2Cl_2$; conversion "b" employs a combination of TEA and $CH_2Cl_2$; conversion "c" employs TsOH in a mixed solvent system comprising THF and water; conversion "d" employs TESCl in a mixed solvent system comprising pyridine and $CH_2Cl_2$; conversion "e" employs ammonium cerium (IV) nitrate in a mixed solvent system comprising acetonitrile and water; and conversion "f" employs a protecting agent, TEA and THF.

Paclitaxels having formula II (see FIG. 1), which have the 2'R, 3'S configuration, may conveniently be prepared by reacting a β-lactam with metal alkoxides of baccatin III derivatives. The ester enolate-imine condensation route to the synthesis of β-lactams is a widely used methodology for the preparation of a variety of β-lactam derivatives (Hart, D. J., and Ha, D.-C., Chem. Rev. 1989, 89(7):1447–1465; ojima, I., Habus, I., Shao, M., Zucco, M., Park, Y. H., Sun, C. M., and Brigaud, T., Tetrahedron, 1992, 48(34): 6985–7012). β-lactams can be prepared from commercially available starting materials, as illustrated by Scheme 5 (see FIG. 6).

The racemic β-lactam 15 may be resolved into the pure enantiomers by recrystalization of the corresponding 2-methoxy-2-(trifluoromethyl) phenylacetic esters. However, the reaction described herein below in which the reaction of metal alkoxide of taxanes with β-lactams is highly diastereoselective. Therefore, the use of a racemic mixture of β-lactams is feasible.

β-Lactam 16 can readily be benzoylated by benzoyl chloride to form the paclitaxel C-13 side chain precursor. Studies have found that the 3'-N-benzoyl group can be replaced by other N-acyl groups with little loss of activity, or even with an increase in activity. Thus, 3'-benzamides provide another site for the introduction of electron affinic groups. The acylation of the β-lactam 16 with a group bearing the nitro group, such as nitrobenzoyl chloride, and nitrophenylchloroformate, can produce the desired precursor for the modification of paclitaxel.

Figure 7:
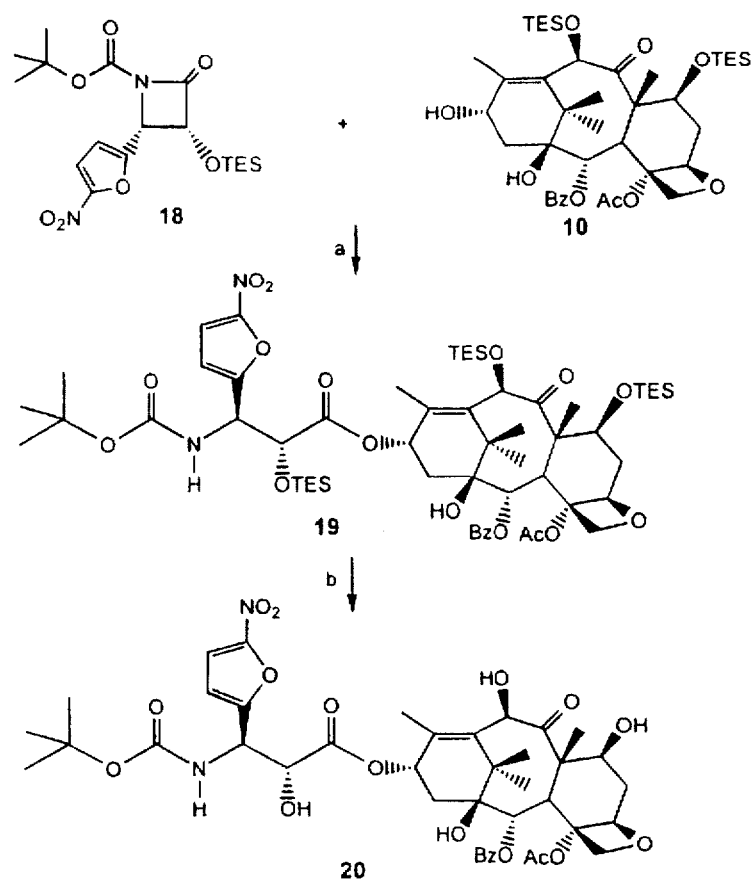
FIG. 7 presents an alternate synthetic scheme (Scheme 6) for the preparation of paclitaxel derivatives. In the scheme, conversion "a" employs a combination of nBuLi and THF; and conversion "b" employs HF in a mixed solvent system comprising pyridine and acetonitrile.

Scheme 6 (see FIG. 7) illustrates the coupling reaction of a β-lactam as a side chain precursor to react with taxane derivatives (structure II as set forth in FIG. 1). First the 7,10-bistriethylsilyl-10-deacetyl baccatin III 10 is deprotonated by a base, such as n-butyllithium, sodium hydride, lithium bis(trimethylsilyl)amide, and the like, in THF at low temperature. Treatment of the C-13 alkoxymetal anion with nitrofuryl β-lactam 18 gives the desired product 19, which is, in turn, subjected to deprotection under standard conditions to give 3'-nitrofuryl paclitaxel analog 20.

Figure 8:
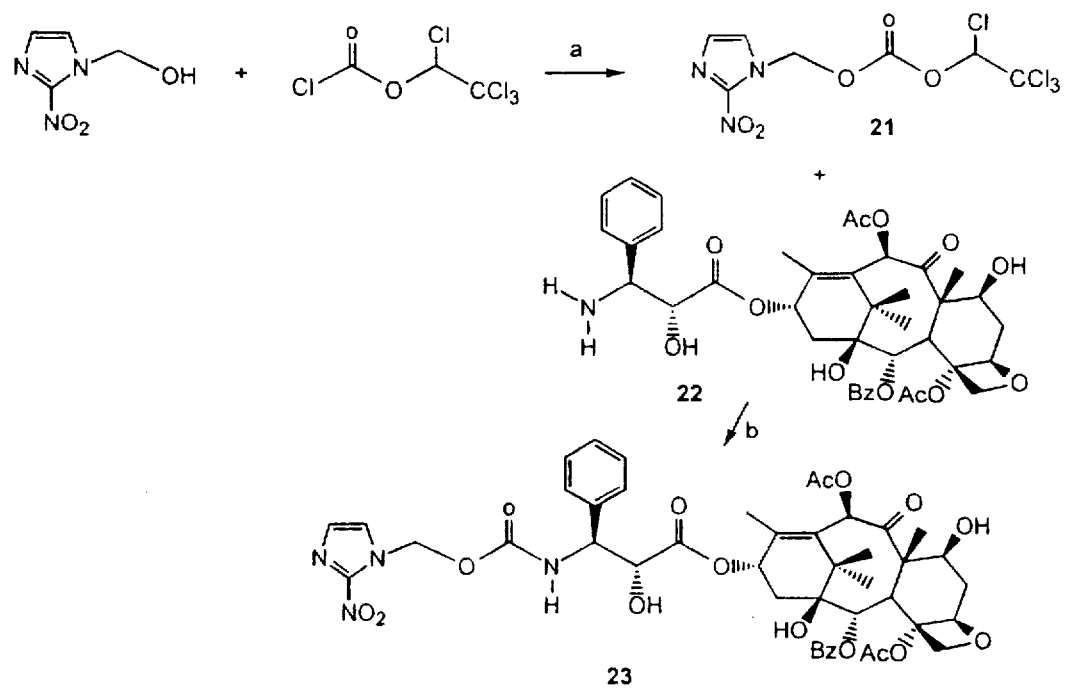
FIG. 8 presents yet another alternate synthetic scheme (Scheme 7) for the preparation of paclitaxel derivatives. In the scheme, conversion "a" is carried out in a mixed solvent system comprising pyridine and $CH_2Cl_2$; and conversion "b" is carried out in pyridine alone.

Nitroimidazole is one of the most effective radiosensitizers. The attachment of a nitroimidazole group at the C-13 side chain should also provide such benefit. As shown in Scheme 7 (see FIG. 8), nitroimidazole can replace the benzoyl group on the 3'-N-amide of paclitaxel. Amino taxoid 22 can be prepared from baccatin III employing a similar procedure, as reported by Commercon et al., in Tetrahedron Lett., 1992, 33:5185–5188. Treatment of 2-nitroimidazole methanol with 1,2,2,2-tetrachloroethyl chloroformate gives the mixed-carbonate 21. Then reaction of the mixed-carbonate 21 with amino-taxoid 22 in pyridine will afford paclitaxel analogue 23.

The invention will now be described in greater detail by reference to the following non-limiting examples.

Example 1 cis-1-(4-Methoxyphenyl)-3-acetoxy-4-(5-nitro-2-furyl)azeditin-2-one

To a solution of p-anisidine (7.00 g, 56.84 mmol) in CH$_2$Cl$_2$ (110 mL) was added 4 molecule sieves (25 g) at room temperature. Then 5-nitro-2-furaldehyde (8.24 g 59.67 mmol) in CH$_2$Cl$_2$ (110 mL) was added dropwise at room temperature. After addition the solution was stirred at room temperature for 3 hr. Removal of 4 molecule sieves left the imine as a yellow solution, which was without further treatment and directly used for next reaction.

To the imine prepared as above was added triethylamine (8.63 g, 85.26 mmol) at −10° C., then added acetoxyacetyl chloride (11.64 g, 85.26 mmol) dropwise within 1 hr at the same temperature. After addition and removal of the cooling bath, the mixture was stirred at room temperature for 3 hr. The mixture was quenched by sodium bicarbonate and extracted by CH$_2$Cl$_2$ (3 ×100 mL). The combined organic layers were washed by sodium bicarbonate, water and saline, dried by Na$_2$SO$_4$. After removal of solvent, a yellow solid (19.52 g) was obtained. Recrystalization in CH$_2$Cl$_2$/hexanes provided the title compound as a yellow crystal (18.52 g).

Example 2 cis-1-(4-Methoxyphenyl)-3-hydroxy-4-(5-nitro-2-furyl)azeditin-2-one

To a solution of cis-1-(4-Methoxyphenyl)-3-acetoxy-4-(5-nitro-2-furyl)azeditin-2-one (9.10 g, 26.23 mmol) in THF-H$_2$O(1:1, 200 mL) at room temperature was added p-toluenesulfonic acid monohydrate (7.50 g, 39.42 mmol). The mixture was heated to reflux until the starting material disappeared, cooled to room temperature, neutralized by NaHCO$_3$ and concentrated to the ½ volume. The mixture was extracted by ethyl acetate (3×80 mL) and combined organic layers were washed by NaHCO$_3$, H$_2$O and brine. After dried (Na$_2$SO$_4$) and concentrated, a brown solid obtained (7.00 g), which was recrystalized from ethyl acetate/hexanes and provided the title compound as a light yellow crystalline solid (5.52 g).

Example 3 cis-1-(4-Methoxyphenyl)-3-triethylsilyloxy-4-(5-nitro-2furyl)azeditin-2-one

To a solution of cis-1-(4-Methoxyphenyl)-3hydroxy-4-(5-nitro-2-furyl)azeditin2-one (5.50 g, 18.09 mmol) in pyridine-CH$_2$cl$_2$ (1:2, 60 mL) at room temperature was added chlorotriethylsilane (3.3 mL, 19.90 mmol). The mixture was stirred for one hour and quenched by addition of methyl alcohol and poured into ethyl acetate/hexanes (100 mL). The organic layer was washed by NaHCO$_3$, H$_2$O, 10% CuSO$_4$, NaHCO$_3$, brine and dried (Na$_2$SO$_4$). Removal of solvents a brown color solid (7.90 g) was given, which was recrystalized from CH$_2$Cl$_2$/hexanes afforded the title compound as a light yellow crystal (6.42 g).

Example 4 cis-3-Triethylsilyloxy-4-(5-nitro-2-furyl)azeditin-2-one

To a solution of cis-1-(4-Methoxyphenyl)-3-triethylsilyloxy-4-(5-nitro-2-furyl)azeditin-2-one (2.50 g, 5.61 mmol) in acetonitrile (150 mL) cooled to −5° C. was added a cooled solution of ammonium cerium(IV) nitrate (15.39 g, 28.08 mmol) in $H_2O$ (60 mL). The mixture was stirred for about one minute and poured into aqueous solution of sodium bicarbonate, and extracted with ethyl acetate. The combined organic layers were washed by sodium bicarbonate, water, brine and dried ($Na_2SO_4$). After removal of the solvents left a light yellow residue which was purified by chromatography eluted with ethyl acetate/hexanes afforded the title compound as a light yellow solid (1.27 g).

Example 5 cis-1(t-Butoxycarbonyl)-3-triethylsilyloxy-4-(5-nitro-2furyl)azeditin-2-one

To a solution of cis-3-triethylsilyloxy-4(5-nitro-2-furyl)azeditin-2-one (1.00 g, 3.33 mmol) in THF (10 mL) was added t-dibutyldicarbonate (1.45 g, 6.65 mmol, triethylamine (1.40 mL, 9.99 mmol) and 4-dimethylaminopyridine) at room temperature. After the starting material disappeared monitored by TLC, the mixture was quenched by aqueous solution of sodium bicarbonate and extracted by ethyl acetate/hexanes (1:5). The combined organic layers were washed by sodium bicarbonate, brine and dried ($Na_2SO_4$). After removal of solvent gave a light yellow oil which was solidified in refrigerator. Separation by column chromatography eluted with ethyl acetate/hexanes (¹/₁₀) afford the desired product as a oil (1.33 g) which was solidified in refrigerator and recrystalized from ether/hexanes to afford the title compound as a white crystalline solid (1.10 g). $^1H$ NMR (500 MHz, $CDCl_3$), δ 7.32 (d, J=3.8 Hz, 1H, H4'), 6.59 (d, J=3.8 Hz, 1H, H3'), 5.14 (d, J =2.5 Hz, 2H, H3, H4), 1.48 (s, 9H, t-butyl), 0.86 (m, 9H, TES), 0.58 (m, 6H, TES).

Example 6

3'-Desphenyl-3'-(5-nitro-2-furyl)-N-debenzoyl-N(t-butoxycarbonyl)taxol

Step 1: To a solution of 7,10-bistriethylsilyl 10-deacetyl baccatin III (50 mg) in tetrahydrofuran was added dropwise lithium bis(trimethylsilyl)amide in tetrahydrofuran or n-butyllithium in hexanes (1.05–1.3 equiv.) at −45° C. After 0.5–1 hour at −45° C., a solution of cis-1(t-Butoxycarbonyl)-3-triethylsilyloxy-4(5-nitro-2-furyl)azeditin-2-one (3–5 equiv) in tetrahydrofuran was added dropwise to the mixture. After addition, the solution was warmed to 0° C. and stirred for an additional hour. The reaction was quenched by acetic acid and extracted by ethyl acetate/hexanes. After evaporation of the organic layer, separation by column chromatography afforded the desired product, 3'-Desphenyl-3'-(5-nitro-2-furyl)-N-debenzoyl-N-(t-butoxycarbonyl)-2',7,10-tristriethylsilyl-taxol (63 mg). Alternatively the mixture can be used without separation in the next step reaction.

Step 2: 3'-Desphenyl-3'-(5-nitro-2-furyl)-N-debenzoyl-N-(t-butoxy-carbonyl)-2',7,10-tristriethyl silyl-taxol (63 mg) was dissolved in acetonitrile, followed by excess pyridine and 48% aqueous hydrogen fluoride or 0.5% HCl in ethanol at 0° C. The mixture was stirred at 0° C. for one hour and then at room temperature until reaction is finished, as monitored by TLC. The mixture was quenched by aqueous sodium bicarbonate and extracted by ethyl acetate. Evaporation of the solvent and purification of the residue by silica gel column chromatography eluted by ethyl acetate/hexanes afforded 54 mg of 3'-Desphenyl-3'-(5-nitro-2-furyl)-N-debenzoyl-N-(t-butoxycarbonyl)taxol. M.p.=174-176° C., $^1H$ NMR (500 MHz, $CDCl_3$), δ 8.11 (d, J=7.5 Hz, 2H, benzoate ortho), 7.6 (t, J=7.5 Hz, 1H, benzoate para), 7.50 (t, J=7.5 Hz, 2H, benzoate meta), 7.31 (d, J=3.5 Hz, 1H, nitrofuryl), 6.58 (d, J=3.5 Hz, 1H, nitrofuryl), 6.26 (t, J=8.8 Hz, 1H, H13), 5.68 (d, J =7.0 Hz, 1H, H2), 5.43 (d, J=9.8 Hz, 1H, NH), 5.36 (d, J=9.8 Hz, 1H, H3'), 5.23 (s, 1H, H10), 4.96 (dd, J=9.5, 1.5 Hz, 1H, H5), 4.79 (br s, 1H, H2'), 4.34 (d, J=8.6 Hz, 1H, H20α), 4.25 (dd, J=10.8, 6.5 Hz, 1H, H7), 4.18 (d, J =8.6 Hz, 1H, H20β), 3.95 (d, J=7.0 Hz, 1H, H3), 3.70 (br s, 1H, 2'OH), 2.60 (ddd, J=14.4, 9.5, 6.5 Hz, 1H, H6α), 2.47 (s, 3H, 4Ac), 2.36 (dd, J=15.0, 8.8 Hz, 1H, H14α), 2.88 (dd, J=15.0, 8.8 Hz, 1H, H14β), 1.94 (s, 3H, Me18), 1.85 (ddd, J=14.4, 10.8, 1.5 Hz, 1H, H6β), 1.76 (s, 3H, Me19), 1.36 (s, 9H, t-butyl), 1.23 (s, 3H, Me17), 1.14 (s, 3H, Me16).

Example 7

3'-Desphenyl-3'-(5-nitro-2-furyl)-N-debenzoyl-N-(isobutoxycarbonyl)-10-deacetyltaxol Step 1: To a solution of 7,10-bistriethylsilyl 10-deacetyl baccatin III (50 mg) in tetrahydrofuran was added dropwise lithium bis(trimethylsilyl)amide in tetrahydrofuran or n-butyllithium in hexanes (1.05–1.3 equiv) at −45° C. After 0.5–1 hour at −45° C., a solution of cis-1-(isobutoxycarbonyl)-3-triethylsilyloxy-4(5-nitro-2-furyl)azeditin-2-one (3–5 equiv) in tetrahydrofuran was added dropwise to the mixture. After addition, the solution was warmed to 0° C. and stirred for an additional hour. The reaction was quenched by acetic acid and extracted by ethyl acetate/hexanes. After evaporation of the organic layer, the separation by column chromatography afforded the desired product, 3'-Desphenyl-3'1'-(5-nitro-2-furyl)-N-debenzoyl-N-(isobutoxycarbonyl)-2',7,10-tristriethylsilyl-taxol (62 mg). Alternatively the mixture can be used without separation in the next step reaction.

Step 2: 3'-Desphenyl-3'-(5-nitro-2-furyl)-N-debenzoyl-N-(isobutoxycarbonyl)-2',7,10-tristriethylsilyl-taxol (62 mg) was dissolved in acetonitrile, followed by excess pyridine and 48 % aqueous hydrogen fluoride or 0.5% HCl in ethanol at 0° C. The mixture was stirred at 0° C. for one hour and then at room temperature until reaction is finished, as monitored by TLC. The mixture was quenched by aqueous sodium bicarbonate and extracted by ethyl acetate. Evaporation of the solvent and purification of the residue by silica gel column chromatography eluted by ethyl acetate/hexanes afforded 45 mg of 3'-Desphenyl-3'-(5-nitro-2-furyl)-N-debenzoyl-N-(isobutoxycarbonyl)-10-deacetyltaxol. M.p.= 157°–159° C. $^1H$ NMR (500 MHz, $CDCl_3$), δ 8.10 (d, J=7.0 Hz, 2H, benzoate ortho), 7.60 (t, J=7.0 Hz, 1H, benzoate para), 7.50 (t, J=7.0 Hz, 2H, benzoate meta), 7.30 (d, J=3.5 Hz, 1H, nitrofuryl), 6.60 (d, J=3.5 Hz, 1H, nitrofuryl), 6.28 (m, 1H, H13), 5.68 (d, J=7.0 Hz, 1H, H2), 5.53 (m, 1H, NH), 5.47 (m, 1H, H3'), 5.22 (s, 1H, H10), 4.95 (dd, J=9.5, 1.5 Hz, 1H, H5), 4.81 (br s, 1H, H2'), 4.32 (d, J=8.5 Hz, 1H, H20 ), 4.25 (m, 1H, H7), 4.18 (d, J=8.5 Hz, 1H, H20β), 3.94 (d, J=7.0 Hz, 1H, H3), 3.78 (m, 2H, isobutyl), 3.70 (br s, 1H, 2'OH), 2.60 (m, 1H, H6α), 2.46 (s, 3H, 4Ac), 2.34 (m, 1H, H14α), 2.24 (m, 1H, H14β), 1.93 (s, 3H, Me18), 1.88 (m, 2H, H6β and isobutyl), 1.76 (s, 3H, Me19), 1.23 (s, 3H, Me17), 1.14 (s, 3H, Me16), 0.83 (d, J=6.7 Hz, 3H, isobutyl), 0.80 (d, J =6.7 Hz, 3H, isobutyl). IR (KBr) 3439, 1722, 1503, 1362, 1252, 821, 719 cm$^{-1}$.

Example 8

3'-Desphenyl-3'-(4-nitrophenyl)-N-debenzoyl-N-(t-butoxy-carbonyl)-10-deacetyltaxol Step 1: To a solution of 7,10-bistriethylsilyl 10-deacetyl baccatin III (50 mg) in tetrahydrofuran was added dropwise lithium bis(trimethylsilyl)amide in tetrahydrofuran or n-butyllithium in hexanes (1.05–1.3 equiv) at −45° C. After 0.5–1 hour at −45° C., a solution of cis-1-(t-butoxycarbonyl)-3-triethylsilyloxy-4-(4-nitro-phenyl)azeditin-2-one (3–5 equiv) in tetrahydrofuran was added dropwise to the mixture. After addition, the solution was warmed to 0° C. and stirred for an additional hour. The reaction was quenched by acetic acid and extracted by ethyl acetate/hexanes. After evaporation of the organic layer, the separation by column chromatography afforded the desired product 3'-Desphenyl-3'-(4-nitrophenyl)-N-debenzoyl-N-(t-butoxycarbonyl)-2',7,10-tristriethylsilyl-taxol (69 mg). Alternatively the mixture can be used without separation in the next step reaction.

Step 2: 3'-Desphenyl-3'-(4-nitrophenyl)-N-debenzoyl-N-(t-butoxycarbonyl)-2',7,10-tristriethylsilyl-taxol (69 mg) was dissolved in acetonitrile, followed by excess pyridine and 48% aqueous hydrogen fluoride or 0.5% HCl in ethanol at 0° C. The mixture was stirred at 0° C. for one hour and then at room temperature until reaction is finished, as monitored by TLC. The mixture was quenched by aqueous sodium bicarbonate and extracted by ethyl acetate. Evaporation of the solvent and purification of the residue by silica gel column chromatography eluted by ethyl acetate/hexanes afforded 44 mg of the title compound. M.p.=184°–186° C. $^1$H NMR (300 MHz, CDCl$_3$) δ 8.26 (d, J=8.7 Hz, 2H, nitrophenyl, ortho), 8.10 (d, J=7.5 Hz, 2H, benzoate ortho), 7.61 (m, 1H, benzoate para) 7.59 (d, J=8.7 Hz, 2H, nitrophenyl meta), 7.49 (t, J=7.5 Hz, 2H benzoate meta), 6.28 (t, J=8.7 Hz, 1H, H13), 5.68 (d, J=6.9 Hz, 1H, H2), 5.53 (d, J=9.9 Hz, 1H, NH), 5.40 (dd, J=9.9, 0.9 Hz, 1H, H3') 5.21 (s, 1H, H10), 4.95 (d, J=8.1 Hz, 1H, H5), 4.67 (br s, 1H, H2') 4.32 (d, J=8.4 Hz, 1H, H20α), 4.23 (m, 2H, H7, 10OH), 4.18 (d, J=8.4 Hz, 1H, H20β), 3.91 (d, J=6.9 Hz, 1H, H3), 3.64 (d, J=3.6 Hz, 1H, 2'OH), 2.59 (m, 1H, H6α), 2.39 (s, 3H, 4Ac), 2.28 (d, J=8.7, 2H, H14), 1.88 (s, 3H, Me18), 1.85 (m, 1H, H6β), 1.76 (s, 3H, Me19), 1.71 (s, 1H, 7OH), 1.58 (s, 1H, 1OH), 1.33 (s, 9H, t-butyl), 1.24 (s, 3H, Me17), 1.14 (s, 3H, Me16). IR (KBr) 3431, 1719, 1529, 1354, 1256, 863, 709, cm$^{-1}$.

Example 9

3'-Desphenyl-3'-(4-nitrophenyl)-N-debenzoyl-N-(isopropoxycarbonyl)-10-deacetyltaxol Step 1: To a solution of 7,10-bistriethylsilyl 10-deacetyl baccatin III (50 mg) in tetrahydrofuran was added dropwise lithium bis(trimethylsilyl)amide in tetrahydrofuran or n-butyllithium in hexanes (1.05–1.3 equiv) at −45° C. After 0.5–1 hour at −45° C., a solution of cis-1-(isopropoxycarbonyl)-3-triethylsilyloxy-4(4-nitrophenyl)azeditin-2-one (3–5 equiv) in tetrahydrofuran was added dropwise to the mixture. After addition, the solution was warmed to 0° C. and stirred for an additional hour. The reaction was quenched by acetic acid and extracted by ethyl acetate/hexanes. After evaporation of the organic layer, the separation by column chromatography afforded the desired product, 3'-Desphenyl-3'-(4-nitrophenyl)-N-debenzoyl-N-(isopropoxycarbonyl)-2',7,10-tristriethylsilyl-taxol (68 mg). Alternatively the mixture can be used without separation in the next step reaction.

Step 2: 3'-Desphenyl-3'-(4-nitrophenyl)-N-debenzoyl-N-(isopropoxycarbonyl)-2',7,10-tristriethylsilyl-taxol (68 mg) was dissolved in acetonitrile, followed by excess pyridine and 48% aqueous hydrogen fluoride or 0.5% HCl in ethanol at 0° C. The mixture was stirred at 0° C. for one hour and then at room temperature until reaction is finished, as monitored by TLC. The mixture was quenched by aqueous sodium bicarbonate and extracted by ethyl acetate. Evaporation of the solvent and purification of the residue by silica gel column chromatography eluted by ethyl acetate/hexanes afforded 43 mg of the title compound. M.p.=178°–179° C. $^1$H NMR (500 MHz, CDCl$_3$), δ 8.26 (d, J=8.7 Hz, 2H, nitrophenyl, ortho), 8.10 (d, J=7.0 Hz, 2H, benzoate ortho), 7.60 (m, 3H, aromatic), 7.49 (t, J=8.9 Hz, 2H benzoate meta), 6.28 (m, 1H, H13), 5.68 (d, J=7.0 Hz, 1H, H2), 5.62 (m, 1H, NH), 5.44 (m, 1H, H3') 5.20 (s, 1H, H10), 4.94 (dd, J=9.9, 1.7 Hz, 1H, H5),4.78 (m, 1H, isopropyl), 4.67 (br s, 1H, H2'), 4.32 (d, J=8.6 Hz, 1H, H20α), 4.22 (m, 1H, H7), 4.19 (d, J=8.6 Hz, 1H, H20β), 3.92 (d, J=7.0 Hz, 1H, H3), 3.70 (br s, 1H, 2'OH), 2.59 (m, 1H, H6α), 2.38 (s, 3H, 4Ac), 2.28 (m, 2H, H14), 1.88 (br s, 4H, Me18, H6β), 1.76 (s, 3H, Me19), 1.24 (d, 6H, isopropyl), 1.16 (s, 3H, Me17), 1.14 (s, 3H, Me16). IR (KBr) 3459, 1722, 1702, 1529, 1356, 1252, 1111, 653, 712 cm$^{-1}$.

Example 10

3'-Desphenyl-3'-(4-nitrophenyl)-N-debenzoyl-N-(isobutoxycarbonyl)-10-deacetyltaxol Step 1:To a solution of 7,10-bistriethylsilyl 10-deacetyl baccatin III (50 mg) in tetrahydrofuran was added dropwise lithium bis(trimethylsilyl)amide in tetrahydrofuran or n-butyllithium in hexanes (1.05–1.3 equiv) at −45° C. After 0.5–1 hour at −45° C., a solution of cis-1-(isobutoxycarbonyl)-3-triethylsilyloxy-4-(4-nitrophenyl) azeditin-2-one (3–5 equiv) in tetrahydrofuran was added dropwise to the mixture. After addition, the solution was warmed to 0° C. and stirred for an additional hour. The reaction was quenched by acetic acid and extracted by ethyl acetate/hexanes. After evaporation of the organic layer, separation by column chromatography afforded the desired product, 3'-Desphenyl-3'-(4-nitrophenyl)-N-debenzoyl-N-(isobutoxycarbonyl)-2',7,10-tristriethylsilyl-taxol (69 mg). Alternatively the mixture can be used without separation in the next step reaction.

Step 2: 3'-Desphenyl-3'-(4-nitrophenyl)-N-debenzoyl-N-(isobutoxycarbonyl)2',7,10-tristriethylsilyl-taxol (69 mg) was dissolved in acetonitrile, followed by excess pyridine and 48% aqueous hydrogen fluoride or 0.5% HCl in ethanol at 0° C. The mixture was stirred at 0° C. for one hour and then at room temperature until reaction is finished, as monitored by TLC. The mixture was quenched by aqueous sodium bicarbonate and extracted by ethyl acetate. Evaporation of the solvent and purification of the residue by silica gel column chromatography eluted by ethyl acetate/hexanes afforded 42 mg of the title compound. M.p. 168=169° C. $^1$H NMR (500 MHz, CDCl$_3$), δ 8.26 (d, J=8.7 Hz, 2H, nitrophenyl, ortho), 8.10 (d, J=7.4 Hz, 2H, benzoate ortho), 7.61 (m, 3H, aromatic), 7.49 (t, J=7.7 Hz, 2H benzoate meta), 6.29 (m, 1H, H13), 5.69 (m, 1H, NH), 5.67 (d, J=6.9 Hz, 1H, H2), 5.44 (m, 1H, H3'), 5.20 (s, 1H, H10), 4.94 (dd, J=9.5, 1.5 Hz, 1H, H5), 4.68 (br s, 1H, H2'), 4.31 (d, J=8.6 Hz, 1H, H20α), 4.22 (m, 1H, H7), 4.19 (d, J=8.6 Hz, 1H, H20β), 3.92 (d, J=6.9 Hz, 1H, H3), 3.73 (m, 2H, isobutyl), 3.70 (br s, 1H, 2'OH), 2.58 (m, 1H, H6α), 2.38 (s, 3H, 4Ac), 2.25 (m, 2H, H14), 1.86 (s, 3H, Me18), 1.82 (m, 2H, H6β and isobutyl), 1.77 (s, 3H, Me19), 1.23(s, 3H, Me17), 1.14 (s, 3H, Me16), 0.81 (d, J=6.7 Hz, 3H, isobutyl), 0.78 (d, J=6.7 Hz, 3H, isobutyl). IR (KBr) 3439, 1722, 1523, 1355, 1252, 1111, 866, 718 cm$^{-1}$.

Example 11

2'-Triethylsilyltaxol

To a solution of taxol (100 mg) in pyridine was added chlorotriethylsilane (3 equiv.) at 0° C. The mixture was stirred at the same temperature for overnight and quenched by sodium bicarbonate and extracted by ethyl acetate. The combined organic solvents were dried ($Na_2SO_4$) and concentrated. The residue was purified by chromatography eluted by ethyl acetate/hexane gave 93 mg desired product.

Example 12

2'-Triethylsilyl-7-(5-nitro-2-furoate)taxol

Step 1: To a solution of 5-nitro-2-furoic acid (5 equiv.) in tetrahydrofuran was added 1,3-dicyclohexyl-carbodiimide (5 equiv.) and catalyzed amount of 4-dimethylaminopyridine and stirred for 5 min. at room temperature. Then 2'-triethylsilyltaxol (50 mg) in tetrahydrofuran was added and the mixture was stirred for 5 hr at room temperature. The mixture was quenched by sodium bicarbonate and extracted by ethyl acetate/hexane. Removal of solvent left a solid which was purified by chromatography gave 2'-triethylsilyl-7-(5-nitro-2-furoate)taxol (51 mg) was obtained.

Step 2: To a solution of 2'-triethylsilyl-7(5-nitro-2-furoate)taxol (51 mg) in acetonitrile and pyridine added aqueous HF or in 0.5% HCl of methanol at room temperature. The mixture was stirred until no starting material was left, as monitored by TLC. After standard workup and purification by chromatography, 46 mg of the title compound was obtained. M.p.=173°–174° C. $^{1}$H NMR (500 MHz, CDCl$_3$), δ 8.12 (d, J=7.4 Hz, 2H, benzoate, ortho), 7.75 (d, J=7.4 Hz, 2H, benzamide ortho), 7.52 (t, J=7.4 Hz, 1H, benzoate para), 7.52–7.36 (m, 10OH, aromatic), 7.30 (d, J=3.7 Hz, 1H, nitrofuryl), 7.12 (d, J=3.7 Hz, 1H, nitrofuryl), 7.03 (d, J=8.8 Hz, 1H, NH), 6.22 (s, 1H, H10), 6.19 (t, J=8.8 Hz, 1H, H13), 5.80 (d, J=9.3 Hz, 1H, H3'), 5.75 (dd, J=10.4, 7.2 Hz, 1H, H7), 5.70 (d, J=6.8 Hz, 1H, H2), 4.98 (d, J=9.5 Hz, 1H, H5), 4.82 (dd, J=5.0, 2.5 Hz, 1H, H2'), 4.35 (d, J=8.6 Hz, 1H, H20α), 4.22 (d, J=8.6 Hz, 1H, H20β), 3.97 (d, J=6.8 Hz, 1H, H3), 3.59 (d, J=5.0 Hz, 1H, 2'OH), 2.73 (m, 1H, H6α), 2.41 (s, 3H, 4Ac), 2.34 (d, J=9.8 Hz, 2H, H14), 2.01 (s, 3H, 10Ac), 1.97 (m, 1H, H6β), 1.91 (s, 3H, Me18), 1.84 (s, 3H, Me19), 1.21 (s, 3H, Me17), 1.15 (s, 3H, Me16). IR (KBr) 3419, 1735, 1548, 1273, 824, 712 cm$^{-1}$.

Example 13

7-(4-Nitrobenzoate)-Taxol

Step 1: To a solution of 4-nitrobenzoic acid (5 equiv.) in tetrahydrofuran was added 1,3-dicyclohexyl-carbodiimide (5 equiv) and a catalytic amount of 4-dimethylaminopyridine and stirred for 5 min at room temperature. Then, 2'-triethylsilyltaxol (50 mg) in tetrahydrofuran was added and the mixture was stirred for 5 hr at room temperature. The mixture was quenched by sodium bicarbonate and extracted by ethyl acetate/hexane (½).

Removal of solvent left a solid which was purified by chromatography to give 2'-triethylsilyl-7-(4-nitro-benzoate) taxol (52 mg).

Step 2: To a solution of 2'-triethylsilyl-7-(4-nitrobenzoate)taxol (51 mg) in acetonitrile and pyridine was added aqueous HF or 0.5% HCl in methanol at room temperature. The mixture was stirred until no starting material was left, as monitored by TLC. After standard workup and purification by chromatography the title compound (44 mg) was obtained. M.p.=168°–170° C. $^{1}$H NMR (300 MHz, CDCl$_3$) δ 8.26 (d, J=8.7 Hz, 2H, nitrobenzoate ortho), 8.14 (d, J=7.2 Hz, 2H, Benzoate ortho), 8.06 (d, J=8.7 Hz, 2H, nitrobenzoate meta), 7.76 (d, J=6.9 Hz, 2H, benzamide ortho), 7.64 (t, J=7.2, 1H, benzoate para), 7.55–7.35 (m, 10H, aromatic) 7.07 (d, J=9.0 Hz, 1H, NH), 6.28 (s, 1H, H10), 6.19 (t, J=8.7 Hz, 1H, H13), 5.81 (d, J=9.0 Hz, 1H, H3'), 5.76 (m, 1H, H7), 5.74 (d, J=6.9 Hz, 1H, H2), 4.99 (d, J=9.0 Hz, 1H, H5), 4.82 (br s, 1H, H2'), 4.36 (d, J=8.4 Hz, 1H, H20α), 4.24 (d, J=8.4 Hz, 1H, H20β), 4.01 (d, J=6.9 Hz, 1H, H3), 3.64 (m, 1H, 2'OH), 2.77 (m, 1H, H6α), 2.42 (s, 3H, 4Ac), 2.36 (d, J=8.7 Hz, 2H, H14), 1.96 (br s, 6H, 10Ac, Me18), 1.92 (m, 1H, H6β), 1.83 (s, 3H, Me18), 1.21 (s, 3H, Me17), 1.18 (s, 3H, Me16). IR (KBr) 3434, 1738, 1529, 1267, 718 cm$^{-1}$.

Example 14

7-[3-(2'-Methyl-4'-nitro-1'-imidazole)proipioate] taxol

Step 1: To a solution of 2-methyl-4-nitro-1-imidazolepropionic acid (5 equiv) in tetrahydrofuran was added 1,3-dicyclohexylcarbodiimide (5 equiv) and a catalytic amount of 4-dimethylaminopyridine and stirred for 5 min. at room temperature. Then 2'-triethylsilyltaxol (50 mg) in tetrahydrofuran was added and the mixture was stirred for 5 hr at room temperature. The mixture was quenched by sodium bicarbonate and extracted by ethyl acetate/hexane. Removal of solvent left a solid which was purified by chromatography to give 2-triethylsilyl-7-|3-(2'-Methyl-4'-nitro-1'-imidazole) propioate| taxol 7-(4-nitrobenzoate)-taxol (53 mg).

Step 2: To a solution of 2'-triethylsilyl-7-|3-(2'-Methyl4'-nitro-1'-imidazole) propioate| taxol 7-(4-nitrobenzoate)-taxol (53 mg) in acetonitrile and pyridine was added aqueous HF or 0.5% HCl in methanol at room temperature. The mixture was stirred until no starting material was left, as monitored by TLC. After standard workup and purification by chromatography, the title compound (48 mg) was obtained. M.p. 157=159° C. $^{1}$H NMR (500 MHz, CDCl$_3$), δ 8.12 (d, J=7.8 Hz, 2H, benzoate, ortho), 7.84 (s, 1H, nitroimidazole), 7.76 (d, J=7.4 Hz, 2H, benzamide ortho), 7.65 (t, J=7.5 Hz, 1H, benzoate para), 7.52–7.36 (m, 10H, aromatic), 7.04 (d, J=8.7 Hz, 1H, NH), 6.19 (t, J=8.9 Hz, 1H, H13), 6.08 (s, 1H, H10), 5.81 (dd, J=9.2, 2.0 Hz, 1H, H3'), 5.66 (d, J=6.8 Hz, 1H, H2), 5.62 (dd, J=10.2, 7.1 Hz, 1H, H7), 4.95 (d, J=9.7 Hz, 1H, H5), 4.82 (br s, 1H, H2'), 4.33 (d, J=8.5 Hz, 1H, H20α), 4.24 (m, 2H, propionate), 4.20 (d, J=8.5 Hz, 1H, H20β), 3.92 (d, J=6.8 Hz, 1H, H3), 3.71 (s, 1H, 2'OH), 2.91 (m, 1H, propionate), 2.68 (m, 1H, propionate), 2.57 (m, 1H, H6α), 2.48 (s, Me on imidazole), 2.40 (s, 3H, 4Ac), 2.35 (d, J=8.9 Hz, 2H, H14), 2.16 (s, 3H, 10Ac), 1.89 (m, 1H, H6β), 1.81 (s, 3H, Me18), 1.80 (s, 3H, Me19), 1.23 (s, 3H, Me17), 1.15 (s, 3H, Me16). IR (KBr) 3437, 1743, 1548, 1515, 1246, 1185, 990, 715 cm$^{-1}$

Example 15

Assay for in Vitro Microtubule Assembly of Paclitaxel Derivatives

Paclitaxel inhibits cell replication in the mitotic phase of the cell cycle by promoting polymerization and stabilization of microtubules. Microtubules are polymers of tubulin in dynamic equilibrium with tubulin heterodimers that are composed of alpha and beta protein subunits. Unlike other antimicrotubule agents, such as the vinca alkaloids (that induce microtubule disassembly), paclitaxel shifts the equilibrium towards microtubule assembly. Paclitaxel-induced microtubules are excessively stable, thereby inhibiting the dynamic reorganization of the microtubule network. The cytotoxic properties of paclitaxel are caused by its unique disruptive effects on microtubules. Thus the activity of taxol or taxol analogs and derivatives may be assessed in vitro by their ability to polymerize tubulin into microtubules (Chaudhary et al. Journal of the American Chemical Society 116:4097–4098 (1994). The polymerization of tubulin is accompanied by a concomitant increase in solution turbidity associated with the formation of microtubules. This increase in turbidity can be assayed spectrophotometrically.

Conditions for tubulin polymerization were determined that did not result in polymerization of tubulin in the absence of taxol at 37° C. Thus, 10 µM tubulin was dissolved in 0.1M MES buffer containing 100 µM GTP and 0.5 mM $MgCl_2$ with a final pH of 6.8. 10 µM tubulin was added to the buffer. 10 µM of taxol (or taxol derivatives) was added to the buffer at 0° C. and the absorbance of the sample measured at 350 nm as the sample temperature increased rapidly to 37° C. with the aid of a circulating water bath connected to the sample chamber of the spectrophotometer. The maximum absorbance of the sample was measured and compared to that of taxol as a control to determine any change in activity of the paclitaxel derivatives. The assay conditions were selected such that taxol (104 µM) would not polymerize tubulin at 10° C., but would promote polymerization at 37° C. For taxol, the values of absorbance (at 350 nm) were 0.0 and 0.295 at 10° C. and 37° C., respectively, while for the taxol derivative synthesized in Example 6 (i.e., 3'-Desphenyl-3'-(5-nitro-2-furyl)-N-debenzoyl-N-(t-butoxycarbonyl)taxol, the absorbances were 0.37 and 0.71 at 10° C. and 37° C., respectively. These data indicate that this derivative is substantially more active in tubulin assembly than unmodified taxol, both at low temperature, as well as at physiological temperatures. Thus, at 37° C., this derivative showed tubulin polymerization activity 2.4 (ratio of absorbances) times that of taxol.

Example 16

Assay for in Vitro Cytotoxicity of Paclitaxel Derivatives

Taxol derivatives were assayed for their cytotoxic activities on tumor cell lines in vitro. The breast adenocarcinoma cell line MCF-7 was chosen as a model for the cytotoxicity assay. The cell line was maintained in RPMI 1640 medium supplemented with 10% fetal bovine serum. For the cell survival experiments, a number of 100 mm petri dishes were plated with $5 \times 10^5$ cells. Exponentially growing cells were exposed to paclitaxel or paclitaxel derivatives at various concentrations 24 hours later. After exposure to paclitaxel and derivatives for various times, the cells were rinsed, trypsinized and washed with medium. The cells were resuspended as single cell suspensions, counted with a particle counter, plated and incubated for macroscopic colony formation. Following a one to two week incubation, the colonies were fixed with methanol/acetic acid, stained with crystal violet and colonies with more than 50 cells counted.

Plating efficiencies for the MCF-7 cell line was found to be in the 45–60% range. The survival was reported as the fraction of cells surviving after exposure to paclitaxel or derivatives thereof. As an example, the cytotoxicity of the derivative synthesized in Example 9, i.e., 3'-Desphenyl-3'-(4-nitrophenyl)-N-debenzoyl-N-(t-butoxycarbonyl)-10-deacetyltaxol, is reported herein. The surviving fraction of MCF-7 cells exposed to 10 nM of paclitaxel or the above derivatives for 24 hours was found to be $6 \times 10^{-2}$ and $2 \times 10^{-3}$, respectively. Thus, the paclitaxel derivative described in Example 9 shows a 30-fold increase in cytotoxicity over unmodified taxol in a breast adenocarcinoma cell line.

Example 17

Assay for Radiosentization of Paclitaxel Derivatives

As discussed in detail elsewhere in this specification, it is expected that derivatives of taxol bearing electron affinic groups (for which various syntheses are set forth herein) will exhibit potent cytotoxic activities when used as radiosensitizers. These dual functional compounds, of value for simultaneous use as chemotherapeutics and radiation sensitizers, will be assayed for their cytotoxic activities in the presence of radiation. For example, cell lines such as the breast cell line referred to in Example 17 can be incubated with these derivatives at different concentrations and for different exposure periods, and the cells irradiated at room temperature with 4 MeV photons from a linear accelerator at a dose rate of 1.5–2 Gy/min. The cells will then be rinsed, trypsinized, counted and plated for macroscopic colony formation immediately after completion of the irradiation. After 1–2 weeks of incubation, the cells will be fixed, stained and colonies counted as described in Example 18. The radiosensitization data will be compared to cytotoxicity data obtained in Example 17 to quantify the added benefit of radiation (in addition to the cytotoxic potential of these compounds), and in order to evaluate the radiosensitization potential of these compounds.

While the invention has been described in detail with reference to certain preferred embodiments thereof, it will be understood that modifications and variations are within the spirit and scope of that which is described and claimed.

That which is claimed is:

1. A dual functional compound having both cytotoxic properties and radiosensitizing properties, wherein said compound is selected from the group consisting of:

3'-Desphenyl-3'-(4-nitrophenyl)-N-debenzoyl-N-(t-butoxy-carbonyl)-10-deacetyltaxol;

3'-Desphenyl-3'-(4-nitrophenyl)-N-debenzoyl-N-(isopropoxycarbonyl)-10-deacetyltaxol;

3'-Desphenyl-3'-(4-nitrophenyl)-N-debenzoyl-N-(isobutoxycarbonyl)-10-deacetyltaxol.

2. A dual functional compound according to claim 1, wherein said compound is 3'-Desphenyl-3'-(4-nitrophenyl)-N-debenzoyl-N-(t-butoxy-carbonyl)-10-deacetyltaxol.

3. A dual functional compound according to claim 1, wherein said compound is 3'-Desphenyl-3'-(4-nitrophenyl)-N-debenzoyl-N-(isopropoxycarbonyl)-10-deacetyltaxol.

4. A dual functional compound according to claim 1, wherein said compound is 3'-Desphenyl-3'-(4-nitrophenyl)-N-debenzoyl-N-(isobutoxycarbonyl)-10-deacetyltaxol.

* * * * *